United States Patent
Ito et al.

(10) Patent No.: US 11,937,785 B2
(45) Date of Patent: Mar. 26, 2024

(54) ENDOSCOPE, DISTAL TIP PIECE, AND METHOD OF MANUFACTURING ENDOSCOPE

(71) Applicant: HOYA CORPORATION, Tokyo (JP)

(72) Inventors: Keiji Ito, Tokyo (JP); Takayoshi Morishima, Tokyo (JP); Kohei Iketani, Tokyo (JP)

(73) Assignee: HOYA CORPORATION, Tokyo (JP)

(*) Notice: Subject to any disclaimer, the term of this patent is extended or adjusted under 35 U.S.C. 154(b) by 500 days.

(21) Appl. No.: 17/253,337

(22) PCT Filed: Dec. 4, 2019

(86) PCT No.: PCT/JP2019/047304
§ 371 (c)(1),
(2) Date: Dec. 17, 2020

(87) PCT Pub. No.: WO2020/116481
PCT Pub. Date: Jun. 11, 2020

(65) Prior Publication Data
US 2021/0259532 A1    Aug. 26, 2021

(30) Foreign Application Priority Data
Dec. 5, 2018 (JP) ................. 2018-228334

(51) Int. Cl.
*A61B 1/00* (2006.01)
*A61B 1/05* (2006.01)

(52) U.S. Cl.
CPC .............. *A61B 1/05* (2013.01); *A61B 1/0011* (2013.01); *A61B 1/00117* (2013.01)

(58) Field of Classification Search
CPC ..... A61B 1/05; A61B 1/0011; A61B 1/00117; A61B 2017/0473; A61B 1/00071
(Continued)

(56) References Cited

U.S. PATENT DOCUMENTS 5,685,823 A    11/1997  Ito et al.
5,830,124 A *  11/1998  Suzuki ............... A61B 1/00124
                                                    600/134
(Continued)

FOREIGN PATENT DOCUMENTS

CN    101461702    6/2009
CN    107149460    9/2017
(Continued)

OTHER PUBLICATIONS

Office Action issued by the China National Intellectual Property Administration (CNIPA) in Chinese Patent Application No. 201980042436.8, dated Mar. 29, 2023.
(Continued)

*Primary Examiner* — Timothy J Neal
*Assistant Examiner* — James Edward Boice
(74) *Attorney, Agent, or Firm* — GREENBLUM & BERNSTEIN, P.L.C.

(57) ABSTRACT

To provide an endoscope or the like that can reuse an image sensor or the like. An endoscope includes: an imaging unit including an image sensor and an optical component that forms an image of light incident from a first end surface on the image sensor; a cable inserted into an insertion portion and having a first end connected to the imaging unit; an exterior cylinder covering a connected portion between the imaging unit and the cable; and a distal tip piece in which a housing portion having a shape fitted with a shape of the exterior cylinder is provided and which is arranged at a distal tip of the insertion portion.

13 Claims, 31 Drawing Sheets

(58) Field of Classification Search
USPC .......................................................... 600/109
See application file for complete search history.

(56) References Cited

U.S. PATENT DOCUMENTS

| | | | | |
|---|---|---|---|---|
| 6,348,035 | B1* | 2/2002 | Takami | G02B 23/2484 |
| | | | | 200/51.09 |
| 7,371,209 | B2 | 5/2008 | Viebach et al. | |
| 2005/0182299 | A1 | 8/2005 | D'Amelio et al. | |
| 2007/0182842 | A1 | 8/2007 | Sonnenschein et al. | |
| 2007/0219409 | A1* | 9/2007 | Shimizu | H01H 36/0013 |
| | | | | 600/101 |
| 2010/0204546 | A1 | 8/2010 | Hassidov et al. | |
| 2015/0238069 | A1* | 8/2015 | Osada | G02B 23/2476 |
| | | | | 600/109 |
| 2017/0059848 | A1* | 3/2017 | Haraguchi | G02B 23/2469 |
| 2017/0251914 | A1 | 9/2017 | Kitano | |
| 2017/0265879 | A1* | 9/2017 | Washburn | A61B 1/317 |
| 2020/0405137 | A1* | 12/2020 | Sørensen | A61B 1/00114 |

FOREIGN PATENT DOCUMENTS

| | | |
|---|---|---|
| EP | 3 257 429 | 12/2017 |
| JP | 64-662 | 1/1989 |
| JP | 05-038324 | 2/1993 |
| JP | 06-254047 | 9/1994 |
| JP | 6-319683 | 11/1994 |
| JP | 7-313439 | 12/1995 |
| JP | 08-24208 | 1/1996 |
| JP | 10-28669 | 2/1998 |
| JP | 2004-141419 | 5/2004 |
| JP | 2004-174242 | 6/2004 |
| JP | 2005-535431 | 11/2005 |
| JP | 2006-114276 | 4/2006 |
| JP | 2007-236812 | 9/2007 |
| JP | 2009-160224 | 7/2009 |
| JP | 2011-104000 | 6/2011 |

OTHER PUBLICATIONS

Jan. 5, 2022 Chinese Office Action issued in corresponding Chinese Patent Application No. 201980042436.8,.
Official Communication issued in International Buereau of WIPO Patent Application No. PCT/JP2019/047304, dated Feb. 18, 2020.
Jul. 19, 2022 Japanese Office Action in corresponding Japanese Patent Application No. 2020-559946 and English translation thereof.
Mar. 1, 2023 German Office Action in corresponding German Application No. 11 2019 006 064.3 and machine translation thereof.
Jul. 4, 2023 German Office Action in corresponding German Application No. 11 2019 006 064.3 and machine translation thereof.

* cited by examiner

ENDOSCOPE, DISTAL TIP PIECE, AND METHOD OF MANUFACTURING ENDOSCOPE

TECHNICAL FIELD

The present invention relates to an endoscope, a distal tip piece, and a method of manufacturing an endoscope.

BACKGROUND ART

After performing endoscopic examination, it is necessary to perform reprocessing such as cleaning, disinfection, and sterilization of a used endoscope. Since the endoscope includes a plurality of narrow pipes such as channels, the reprocessing requires much work and time.

A so-called disposable endoscope, which is used once and then discarded, has been proposed (Patent Literature 1).

CITATION LIST

Patent Literature
Patent Literature 1: JP H5-38324 A

SUMMARY OF INVENTION

Technical Problem

In a normal endoscope that is reprocessed and used after use, a small and high-definition image sensor and imaging lens are used. The image sensor and imaging lens are expensive. Therefore, it is difficult to adopt an image sensor and imaging lens having the same specifications as a normal endoscope for a disposable endoscope. Since a high image quality cannot be obtained with an endoscope using a relatively inexpensive image sensor and imaging lens, it is difficult to perform reliable endoscopic diagnosis and endoscopic treatment.

In one aspect, an object is to provide an endoscope or the like that can reuse an image sensor or the like.

Solution to Problem

An endoscope includes: an imaging unit including an image sensor and an optical component that forms an image of light incident from a first end surface on the image sensor; a cable inserted into an insertion portion and having a first end connected to the imaging unit; an exterior cylinder covering a connected portion between the imaging unit and the cable; and a distal tip piece in which a housing portion having a shape fitted with a shape of the exterior cylinder is provided and which is arranged at a distal tip of the insertion portion.

Advantageous Effects of Invention

In one aspect, it is possible to provide an endoscope or the like that can reuse an image sensor or the like.

DESCRIPTION OF EMBODIMENTS

[First Embodiment]

Figure 1:
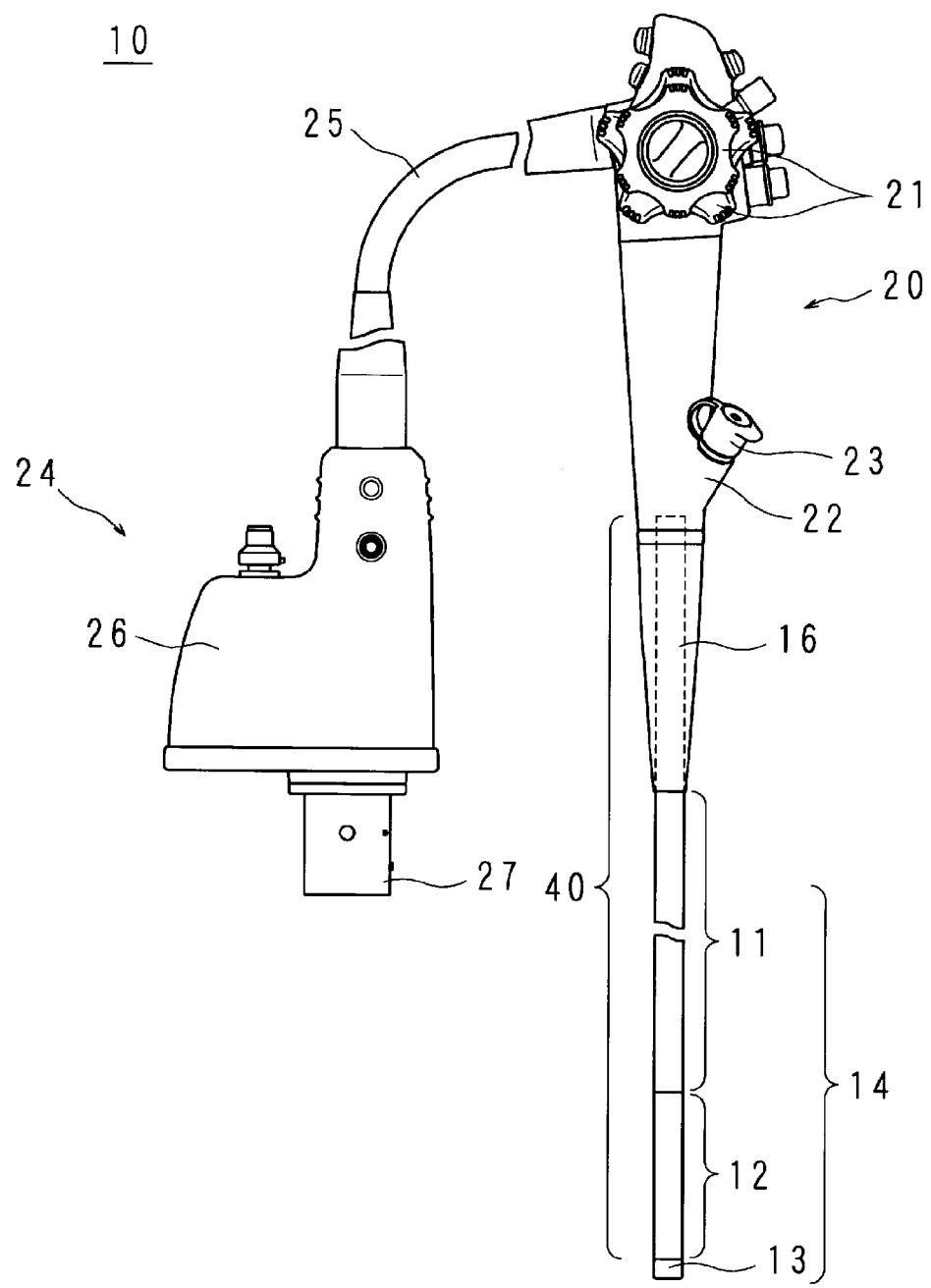
FIG. 1 is an exterior view of an endoscope.

FIG. 1 is an exterior view of an endoscope 10. The endoscope 10 of the present embodiment is a flexible scope for a gastrointestinal tract. The endoscope 10 includes an insertion portion 14, an operation unit 20, a universal cord 25, and a connector unit 24. The operation unit 20 includes a bending knob 21 and a channel inlet 22. A forceps plug 23 having an insertion port to insert a treatment tool or the like is fixed to the channel inlet 22.

The insertion portion 14 is long and has one end connected to the operation unit 20 via a bend preventing portion 16. The insertion portion 14 includes a soft portion 11, a bending section 12, and a distal tip piece 13 in the order from the operation unit 20 side. The bending section 12 is bent according to an operation of the bending knob 21.

In the present embodiment, the soft portion 11 and the bending section 12 are implemented by one multi-lumen tube 40. The multi-lumen tube 40 is a tube that a plurality of through-holes penetrate in a longitudinal direction. In the multi-lumen tube 40, a portion that is relatively easy to bend and a portion that is relatively difficult to bend are integrally molded. The portion that is relatively easy to bend is formed of a resin material having a low hardness. The portion that is relatively difficult to bend is formed of a resin material having a high hardness. The bending section 12 is formed by the portion formed of the resin material having a low hardness, and the soft portion 11 is formed by the portion formed of the resin material having a high hardness.

By implementing the soft portion 11 and the bending section 12 with one multi-lumen tube 40, the work and time required for assembly can be significantly reduced. Therefore, it is possible to provide the endoscope 10 suitable for single use.

In the following description, a longitudinal direction of the insertion portion 14 is referred to as an insertion direction. Similarly, a side close to the operation unit 20 along the insertion direction is referred to as an operation unit side, and a side distant from the operation unit 20 is referred to as a distal tip side. For each component, the expressions such as the operation unit side and the distal tip side are used according to the orientation when attached to the endoscope 10.

The universal cord 25 is long, and has a first end connected to the operation unit 20 and a second end connected to the connector unit 24. The connector unit 24 is covered with a substantially rectangular parallelepiped connector case 26. A scope connector 27 protrudes from one surface of the connector case 26. The connector unit 24 is connected to a processor for an endoscope, an air supply/water supply device, and the like (not illustrated).

Figure 2:
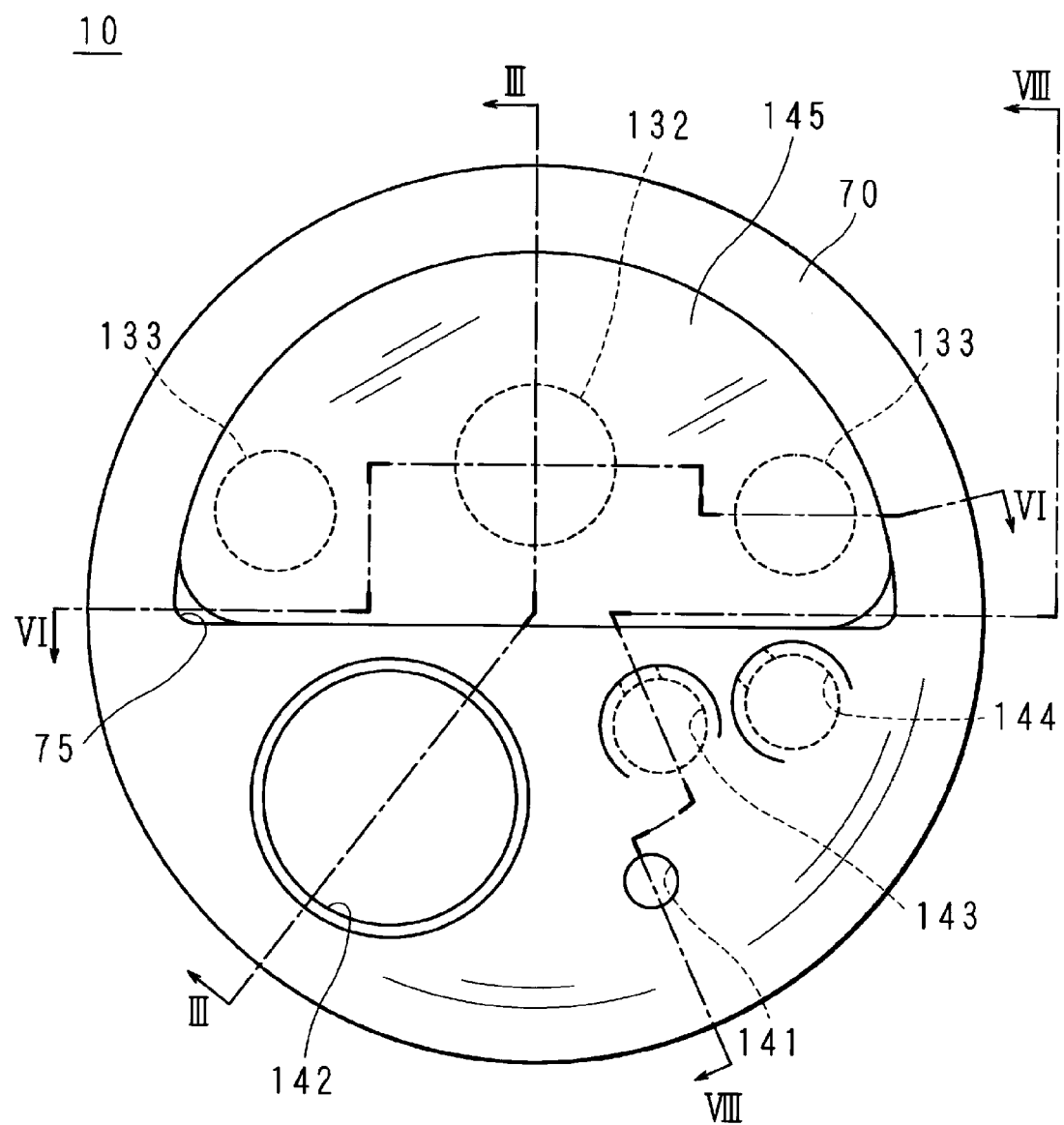
FIG. 2 is an explanatory view for describing a configuration of the endoscope.

FIG. 2 is an explanatory view for describing a configuration of the endoscope 10. FIG. 2 illustrates a state where the insertion portion 14 is viewed from the distal tip side. A jet outlet 141, a channel outlet 142, an air supply nozzle 143, a water supply nozzle 144, and a window plate 145 are provided in an end surface of the insertion portion 14.

The end surface of the insertion portion 14 is substantially circular. The window plate 145 is provided in the upper half of the end surface in FIG. 2. The window plate 145 is translucent. Behind the window plate 145, an observation window 132 and two illumination windows 133 arranged on the left and right sides of the observation window 132 are provided.

The channel outlet 142 is provided at the lower left side in FIG. 2. The air supply nozzle 143 and the water supply nozzle 144 are provided on the right side of the observation window 132 so that an outlet of each of the air supply nozzle 143 and the water supply nozzle 144 faces the observation window 132. The jet outlet 141 is arranged below the air supply nozzle 143.

Figure 3:
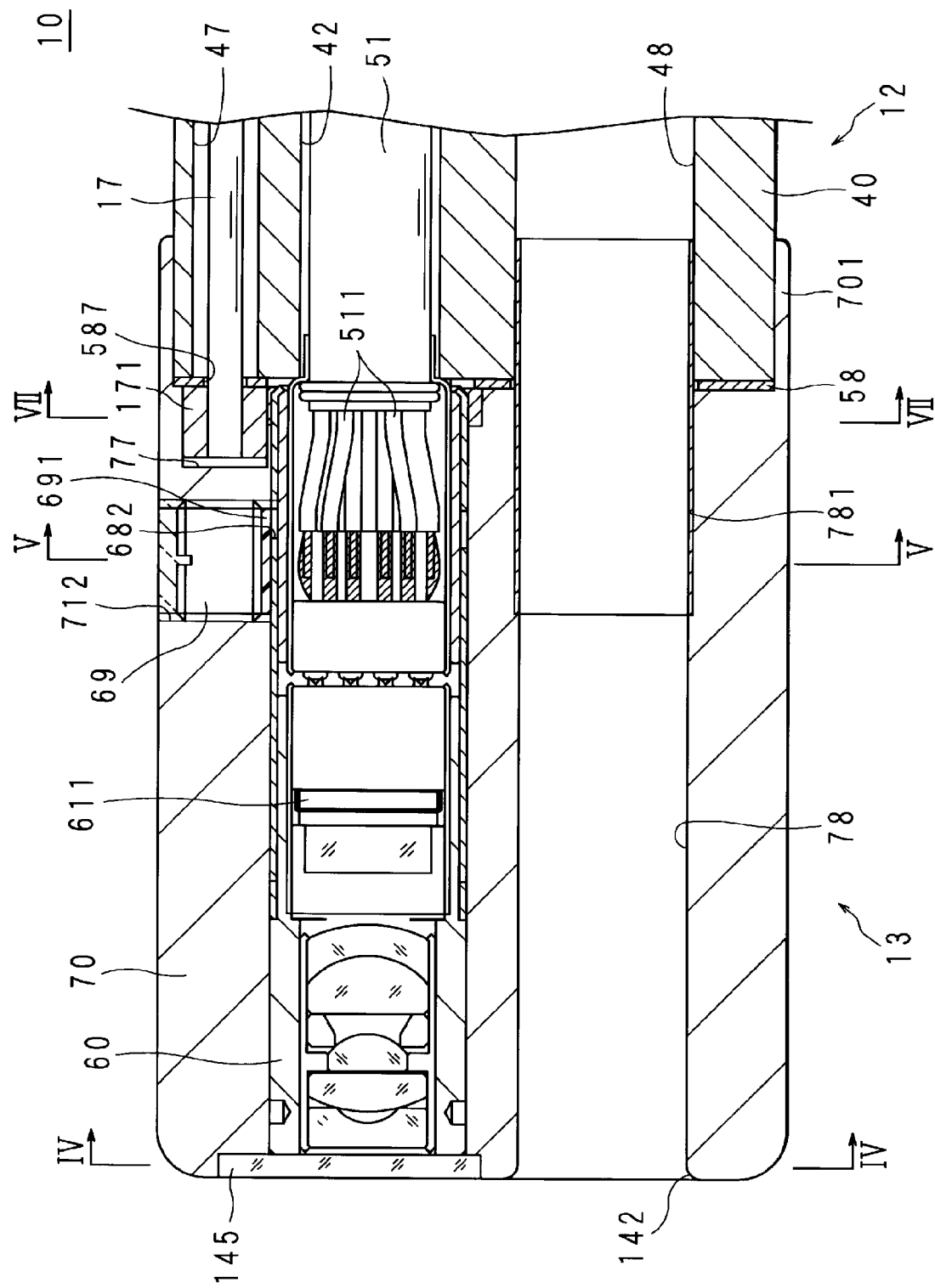
FIG. 3 is a partial cross-sectional view of the endoscope taken along line III-III of FIG. 2.
Figure 4:
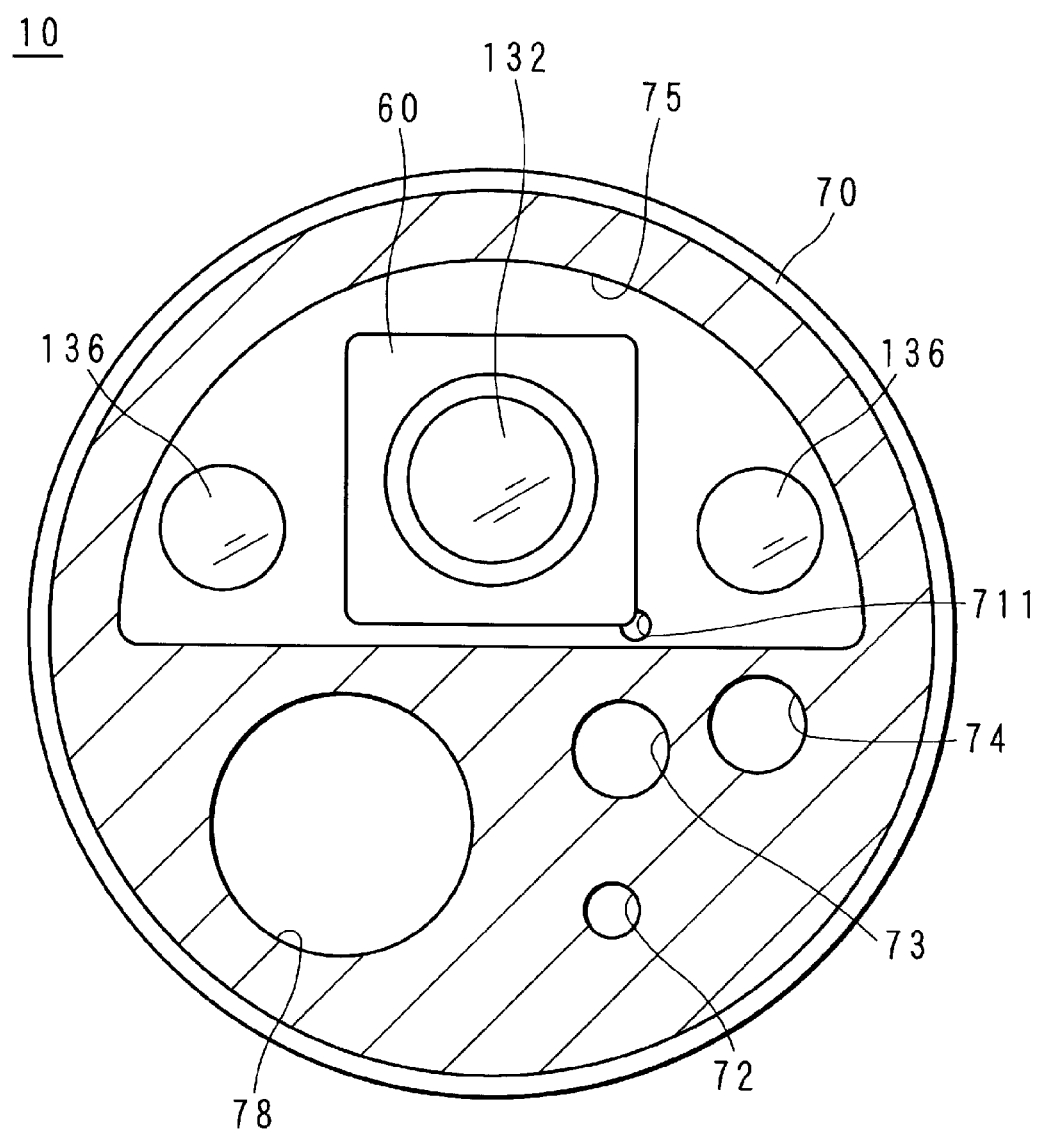
FIG. 4 is a cross-sectional view of the endoscope taken along line IV-IV in FIG. 3.
Figure 5:
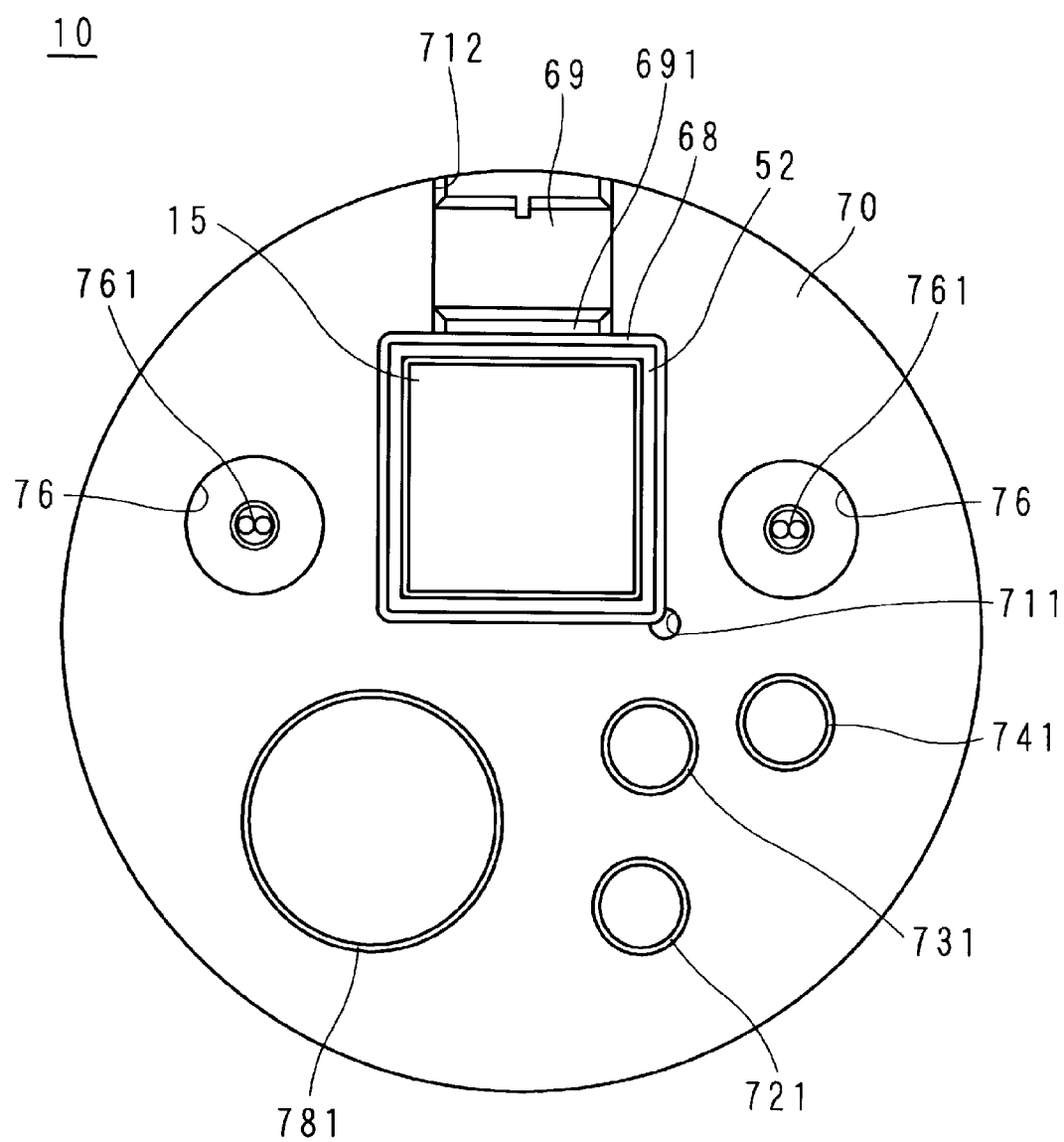
FIG. 5 is a cross-sectional view of the endoscope taken along line V-V of FIG. 3.

FIG. 3 is a partial cross-sectional view of the endoscope 10 taken along line III-III of FIG. 2. FIG. 4 is a cross-sectional view of the endoscope 10 taken along line IV-IV in FIG. 3. FIG. 5 is a cross-sectional view of the endoscope 10 taken along line V-V of FIG. 3.

The distal tip piece 13 including a substantially cylindrical distal tip frame 70 is attached to the distal tip side of the multi-lumen tube 40 by any means such as bonding. Details of the configuration of the distal tip piece 13 will be described later. A disc-shaped abutting plate 58 having a plurality of through-holes is arranged between an end surface of the multi-lumen tube 40 and the distal tip frame 70. Details of the configuration of the abutting plate 58 will be described later.

A window plate frame 75, which is substantially semicircular and recessed to a uniform depth, is provided on an end surface of the distal tip frame 70 on the distal tip side. The window plate 145 is fitted into the window plate frame 75 and attached to the distal tip frame 70 by any means such as bonding or ultrasonic welding.

As illustrated in FIG. 2, gaps are provided between the edge of the window plate 145 and the edge of the window plate frame 75 at opposite ends of straight portions of the window plate 145 and the window plate frame 75. Therefore, recessed portions are formed at the opposite ends of the straight portion of the window plate frame 75 in the end surface of the insertion portion 14.

An imaging/cable unit 15 (see FIG. 11) including the observation window 132 on the distal tip side is arranged on the operation unit side of the window plate 145. The imaging/cable unit 15 includes an image sensor 611 and a cable bundle 51, forms, on the image sensor 611, an image of light incident from an image capturing window, and converts an optical image into an electric signal. The imaging/cable unit 15 has a substantially prismatic shape inside the distal tip piece 13, and is thicker than the cable bundle 51. Details of the configuration of the imaging/cable unit 15 will be described later.

The cable bundle 51 is a bundle of a plurality of cable strands 511, supplies power to the image sensor 611, and transmits/receives a signal. The cable bundle 51 is inserted into a cable hole 42 penetrating the multi-lumen tube 40, and is connected to the scope connector 27 via the operation unit 20, the universal cord 25, and the connector unit 24.

A communication hole 712 including a female screw is provided in a side surface of the distal tip frame 70. The imaging/cable unit 15 is fixed to the distal tip frame 70 by a fixing screw 69 screwed into the communication hole 712. Note that a protection sheet 691 that prevents the imaging/cable unit 15 from being damaged is arranged between a distal tip of the fixing screw 69 and the surface of the imaging/cable unit 15. A head portion of the fixing screw 69 is covered with an adhesive that is soft even after curing, such as a silicone-based adhesive.

The channel outlet 142 is connected to the channel inlet 22 via a channel hole 78 penetrating the distal tip frame 70, a channel pipe 781, a channel hole 48 penetrating the multi-lumen tube 40, and a tube (not illustrated).

By inserting a treatment tool (not illustrated) from the channel inlet 22, a distal tip of the treatment tool protrudes from the channel outlet 142. The treatment tool is used for endoscopic treatment procedures such as removal of polyps.

Figure 6:
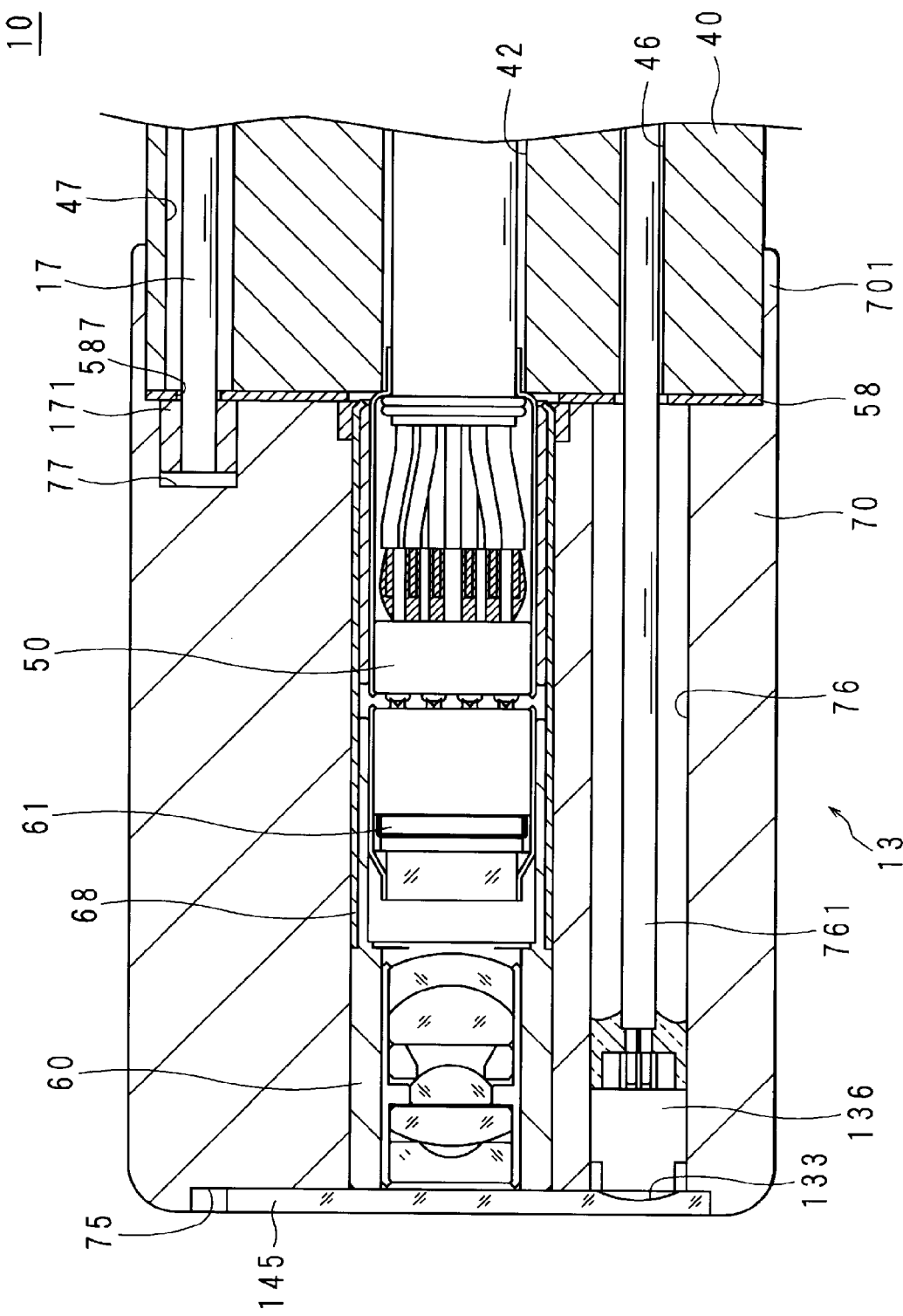
FIG. 6 is a partial cross-sectional view of the endoscope taken along line VI-VI of FIG. 2.

FIG. 6 is a partial cross-sectional view of the endoscope 10 taken along line VI-VI of FIG. 2. Note that, in FIG. 6, the distal tip side is shown on the left side and the operation unit side is shown on the right side as in FIG. 3. The illumination window 133 is a concave surface formed in a surface of the window plate 145 on the operation unit side. A light emitting element 136 is attached to the inside of an illumination hole 76 provided on the operation unit side of the illumination window 133 by any means such as bonding. The illumination window 133 widens an irradiation angle of illumination light emitted from the light emitting element 136 to illuminate a predetermined range.

An illumination cable 761 that supplies power to the light emitting element 136 is connected to the light emitting element 136. The illumination cable 761 is inserted into the illumination hole 76 and an illumination hole 46 penetrating the multi-lumen tube 40, and is connected to the scope connector 27 via the operation unit 20, the universal cord 25, and the connector unit 24.

Figure 7:
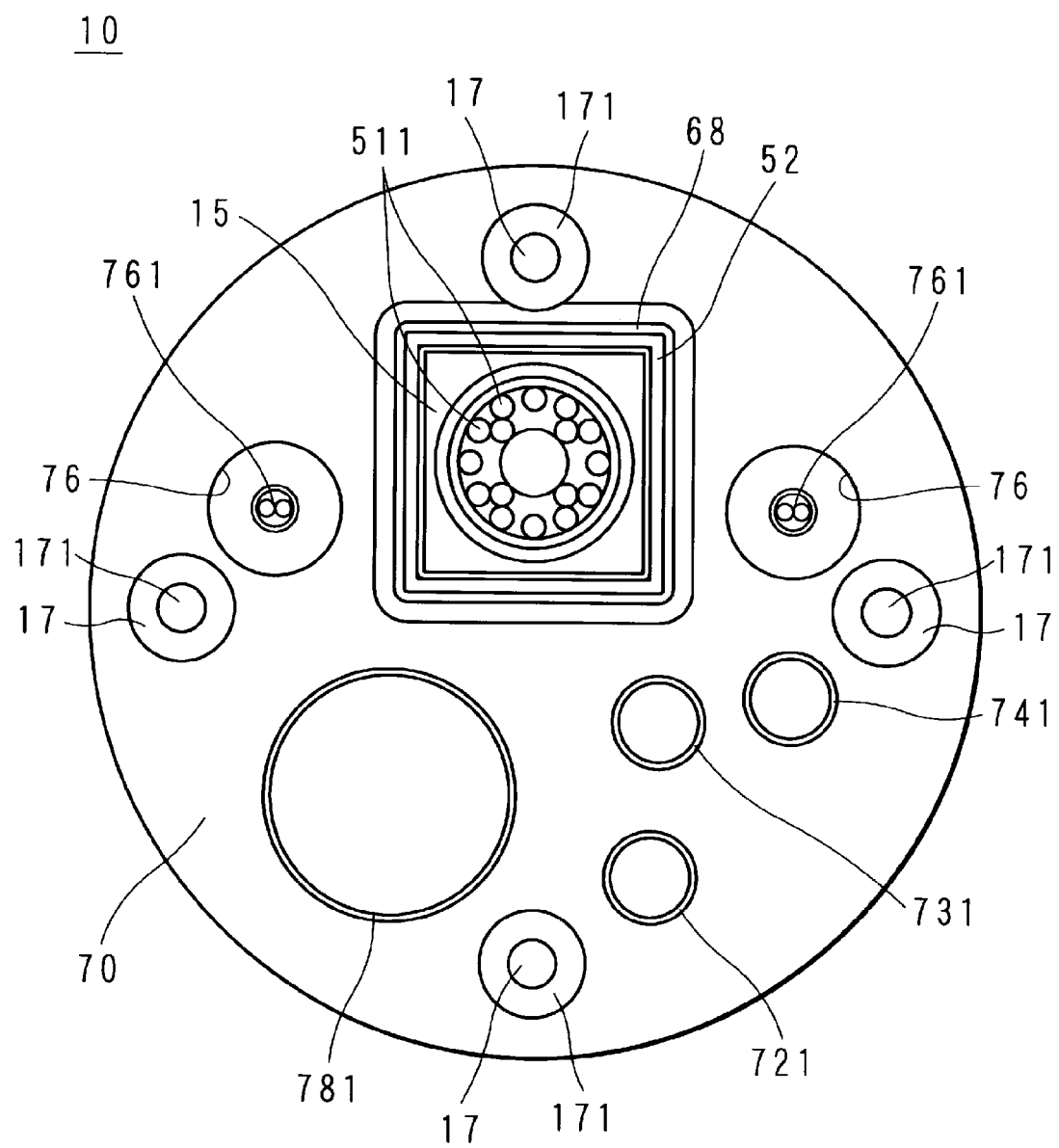
FIG. 7 is a cross-sectional view of the endoscope taken along line VII-VII of FIG. 3.

FIG. 7 is a cross-sectional view of the endoscope 10 taken along line VII-VII of FIG. 3. Four bending wires 17 are arranged in the vicinity of an outer circumference of the insertion portion 14 in a substantially even distribution. An annular cylindrical bending wire stopper 171 is fixed to one end of the bending wire 17 by any means such as brazing, bonding, or caulking.

The bending wire stopper 171 is housed in a wire stopper hole 77 provided in the distal tip frame 70. The other end of the bending wire 17 penetrates a wire hole 587 provided in the abutting plate 58 and the bending wire hole 47 penetrating the multi-lumen tube 40, and is connected to the bending knob 21 inside the operation unit 20.

When a user operates the bending knob 21, one or two adjacent bending wires 17 are pulled toward the operation unit side. As illustrated in FIG. 6, since the bending wire stopper 171 is thicker than the wire hole 587, the bending wire stopper 171 does not move even when it is pulled strongly and stays in the wire stopper hole 77.

As described above, the bending section 12 is formed of a resin material having a low hardness, and is more easily bent than the soft portion 11. Therefore, when the bending wire 17 is pulled, the bending section 12 is bent.

Figure 8:
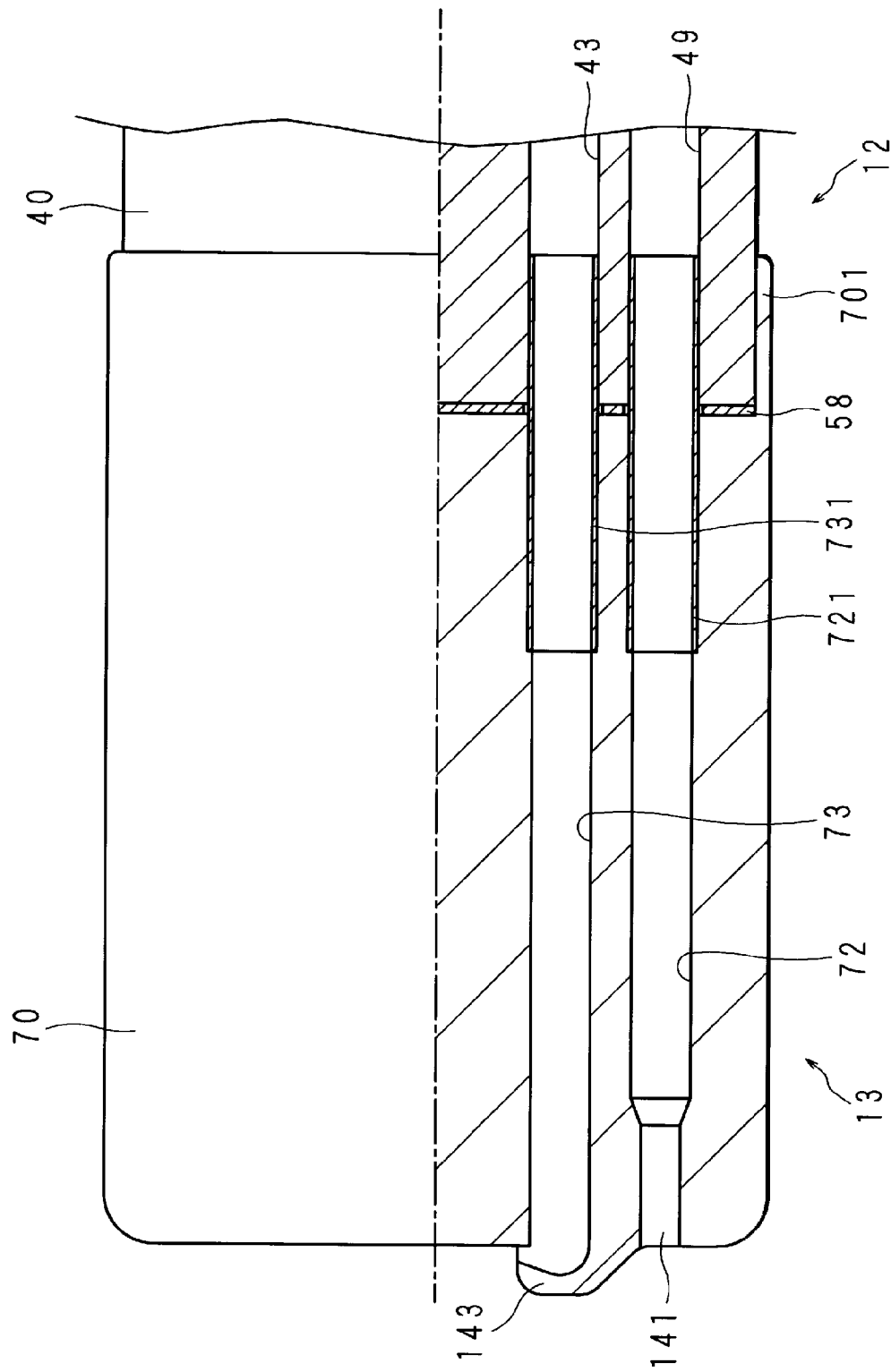
FIG. 8 is a partial half cross-sectional view of the endoscope taken along line VIII-VIII of FIG. 2.

FIG. 8 is a partial half cross-sectional view of the endoscope 10 taken along line VIII-VIII of FIG. 2. The air supply nozzle 143 is implemented by a protrusion provided around an air supply hole 73 penetrating the distal tip frame 70. The air supply nozzle 143 closes a distal tip of the air supply hole 73, and only a portion facing the observation window 132 is open as indicated by a broken line in FIG. 2.

The air supply hole 73 is connected to an air supply/water supply device via an air supply pipe 731, an air supply hole 43 penetrating the multi-lumen tube 40, and a tube (not illustrated). The air supply from the air supply/water supply device is discharged from the air supply nozzle 143 toward the observation window 132.

Although not illustrated, the water supply nozzle 144 also has a vertical cross-sectional shape similar to that of the air supply nozzle 143, and is connected to the air supply/water supply device via a water supply pipe 741, a water supply hole penetrating the multi-lumen tube 40, and a tube (not illustrated). The water supplied from the air supply/water supply device is discharged from the water supply nozzle 144 toward the observation window 132. The air supply nozzle 143 and the water supply nozzle 144 are used, for example, to clean the observation window 132 during endoscopic examination.

The jet outlet 141 is connected to the air supply/water supply device via a jet hole 72 penetrating the distal tip frame 70, a jet pipe 721, a jet hole 49 penetrating the multi-lumen tube 40, and a tube (not illustrated). The distal tip side of the jet hole 72 is formed to be thin. The water is supplied from the air supply/water supply device at an increased speed in the jet hole 72 and is vigorously discharged to the distal tip side. The water supply from the jet outlet 141 is used to wash away residues, mucus, blood, and the like from an observation target site.

Figure 9:
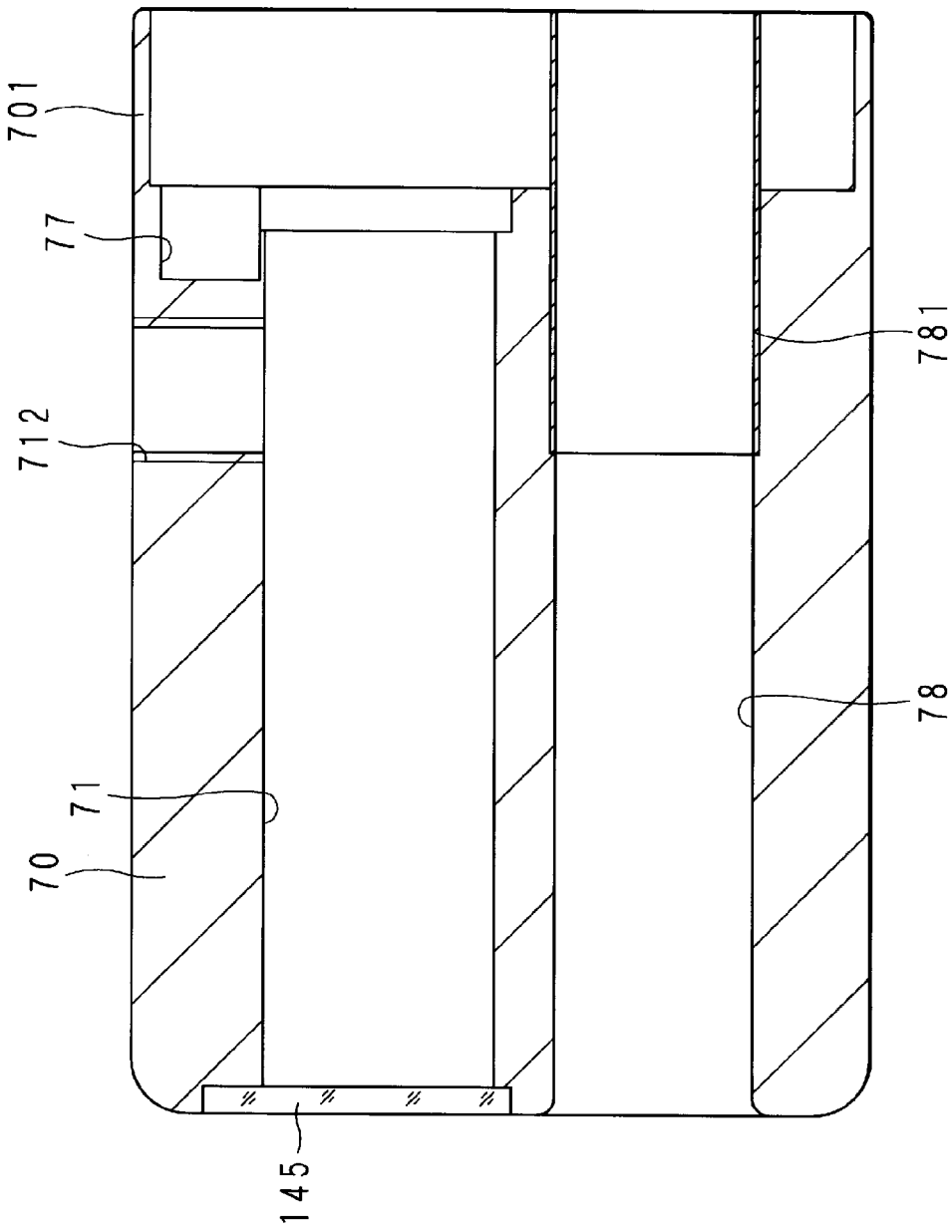
FIG. 9 is a cross-sectional view of a distal tip piece.
Figure 10:
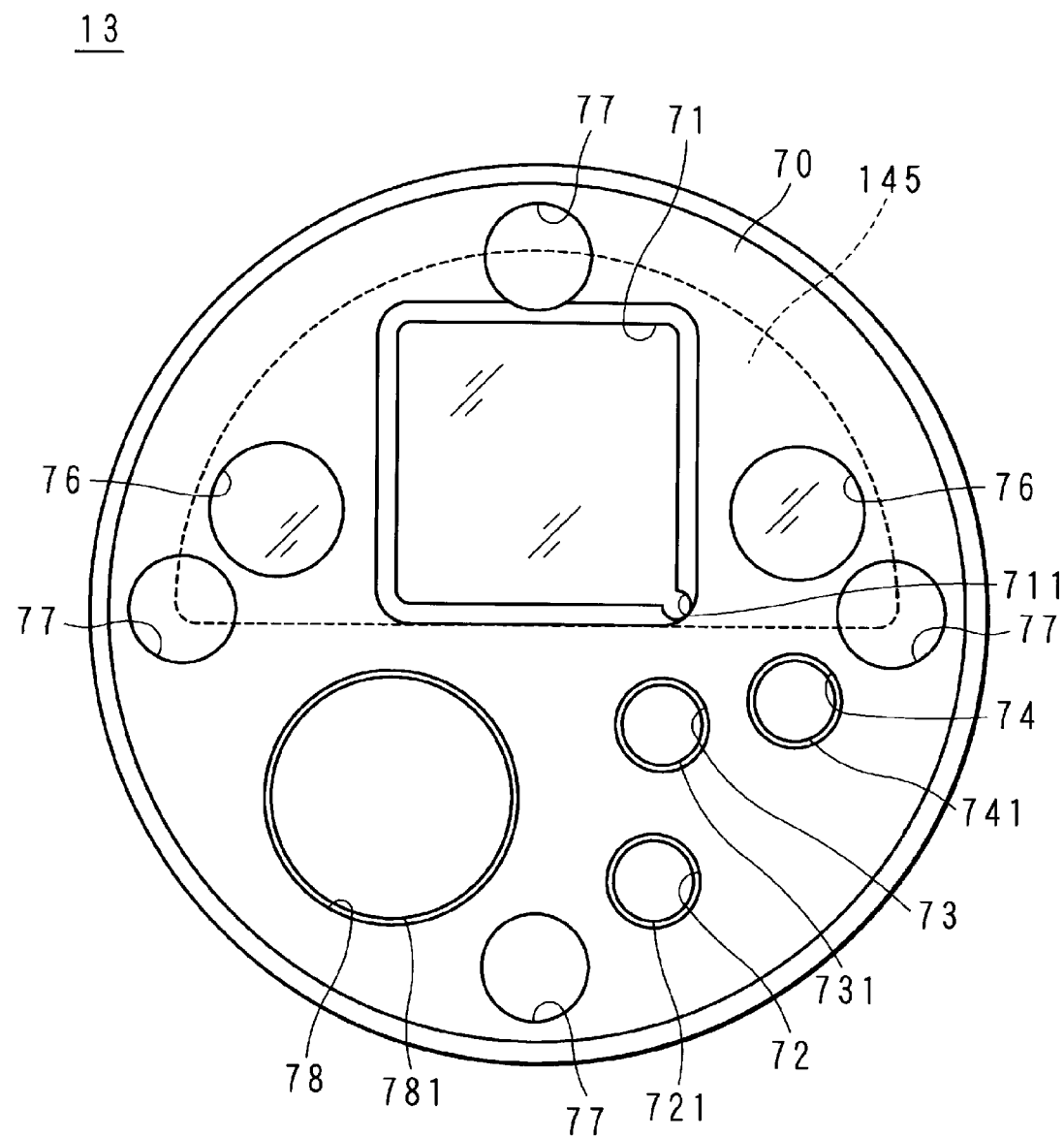
FIG. 10 is a side view of the distal tip piece as viewed from an operation unit side.

FIG. 9 is a cross-sectional view of the distal tip piece 13. In FIG. 9, the left side is the distal tip side and the right side is the operation unit side. FIG. 10 is a side view of the distal tip piece 13 as viewed from the operation unit side. The distal tip piece 13 includes the distal tip frame 70, the window plate 145, the channel pipe 781, the jet pipe 721, the air supply pipe 731, and the water supply pipe 741.

As described above, the distal tip frame 70 has a substantially cylindrical shape. A distal tip frame edge 701 protrudes along an outer circumference from an end surface of the distal tip frame 70 on the operation unit side. The outer circumference of the distal tip frame 70 on the distal tip side is smoothly rounded.

The window plate 145 is attached to the window plate frame 75 provided in the end surface of the distal tip frame 70 on the distal tip side. A square hole 71 into which the imaging/cable unit 15 is inserted penetrates at a position corresponding to the observation window 132 of the distal tip frame 70. An edge of the square hole 71 on the operation unit side has a step and is formed to be thick. An air hole 711 is provided at the lower right corner of the square hole 71 in FIG. 10. The air hole 711 penetrates the distal tip frame 70 so as to be parallel to the square hole 71.

The communication hole 712 that communicates with the square hole 71 from the side surface of the distal tip frame 70 is provided. An inner surface of the communication hole 712 is a female screw. An inner wall of the square hole 71 and the communication hole 712 are substantially perpendicular to each other. The illumination hole 76 to which the light emitting element 136 is attached penetrates at a position corresponding to the illumination window 133 of the distal tip frame 70.

An outlet of the jet hole 72 penetrating the distal tip frame 70 while being tapered forms the jet outlet 141. An end surface of the channel hole 78 penetrating the distal tip frame 70 on the distal tip side forms the channel outlet 142. The air supply nozzle 143 protrudes from the distal tip side of the air supply hole 73 penetrating the distal tip frame 70. The water supply nozzle 144 protrudes from the distal tip side of the water supply hole 74 penetrating the distal tip frame 70.

The jet hole 72, the air supply hole 73, the water supply hole 74, and the channel hole 78 each have a step on the operation unit side to form a large diameter portion. The jet pipe 721 is fixed to the large diameter portion of the jet hole 72 by an arbitrary method such as bonding. An inner surface of the jet pipe 721 is smoothly continuous with an inner surface of the jet hole 72.

The air supply pipe 731 is fixed to the large diameter portion of the air supply hole 73 by an arbitrary method such as bonding. An inner surface of the air supply pipe 731 is smoothly continuous with an inner surface of the air supply hole 73. The water supply pipe 741 is fixed to the large diameter portion of the water supply hole 74 by an arbitrary method such as bonding. An inner surface of the water supply pipe 741 is smoothly continuous with an inner surface of the water supply hole 74. The channel pipe 781 is fixed to the large diameter portion of the channel hole 78 by an arbitrary method such as bonding. An inner surface of the channel pipe 781 is smoothly continuous with an inner surface of the channel hole 78.

The lengths of the jet pipe 721, the air supply pipe 731, the water supply pipe 741, and the channel pipe 781 are substantially the same, and end surfaces thereof on the operation unit side are substantially coplanar with the end surface of the distal tip frame edge 701.

Four wire stopper holes 77 each having a circular cross section are arranged in the vicinity of the outer circumference of the end surface of the distal tip frame 70 on the operation unit side in a substantially even distribution.

Figure 11:
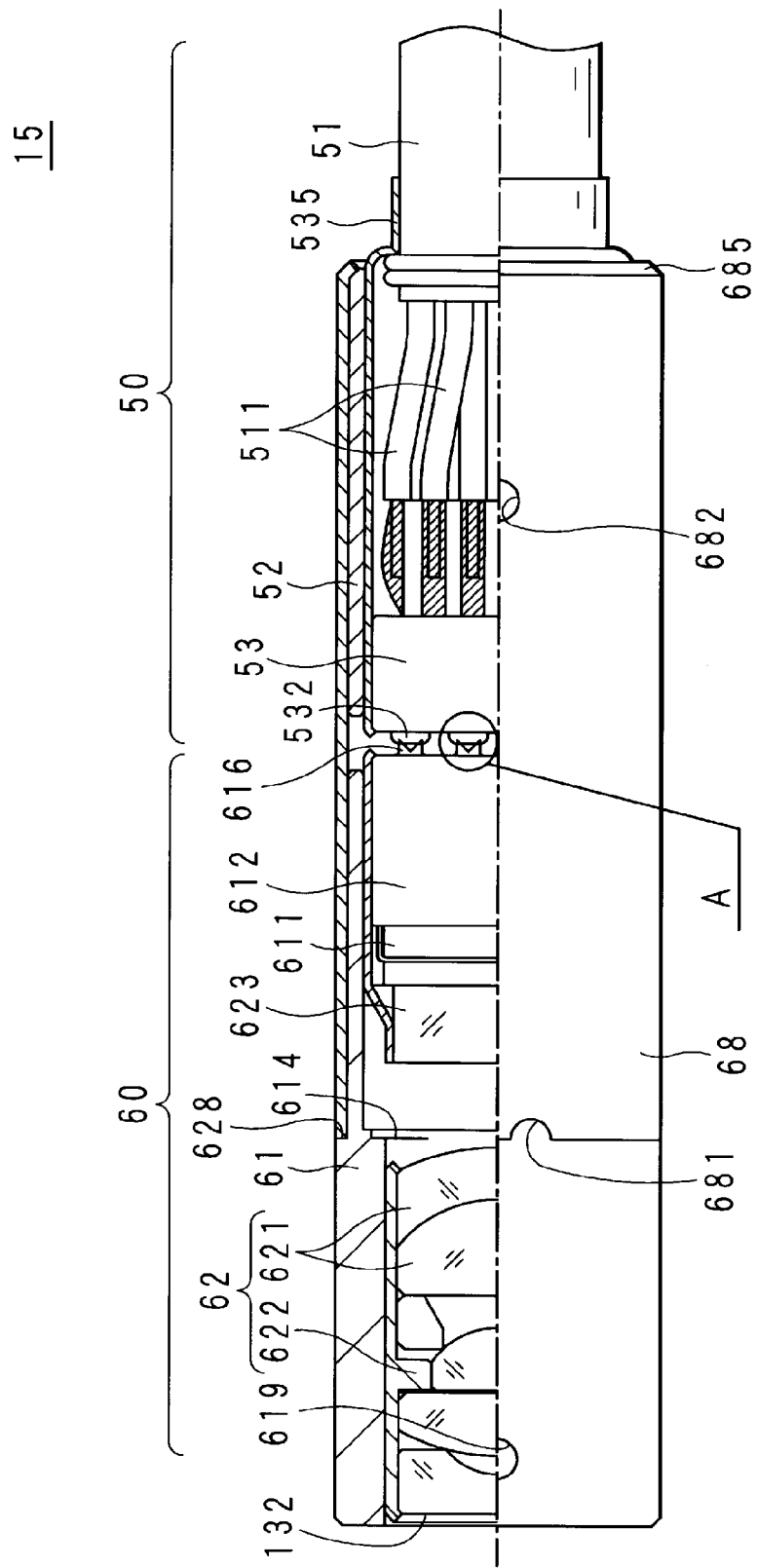
FIG. 11 is a half cross-sectional view of an imaging/cable unit.

FIG. 11 is a half cross-sectional view of the imaging/cable unit 15. In FIG. 11, the left side is the distal tip side and the right side is the operation unit side. The imaging/cable unit 15 is configured by connecting a cable assembly 50, which will be described later, and an imaging unit 60 by using an exterior cylinder 68.

Figure 12:
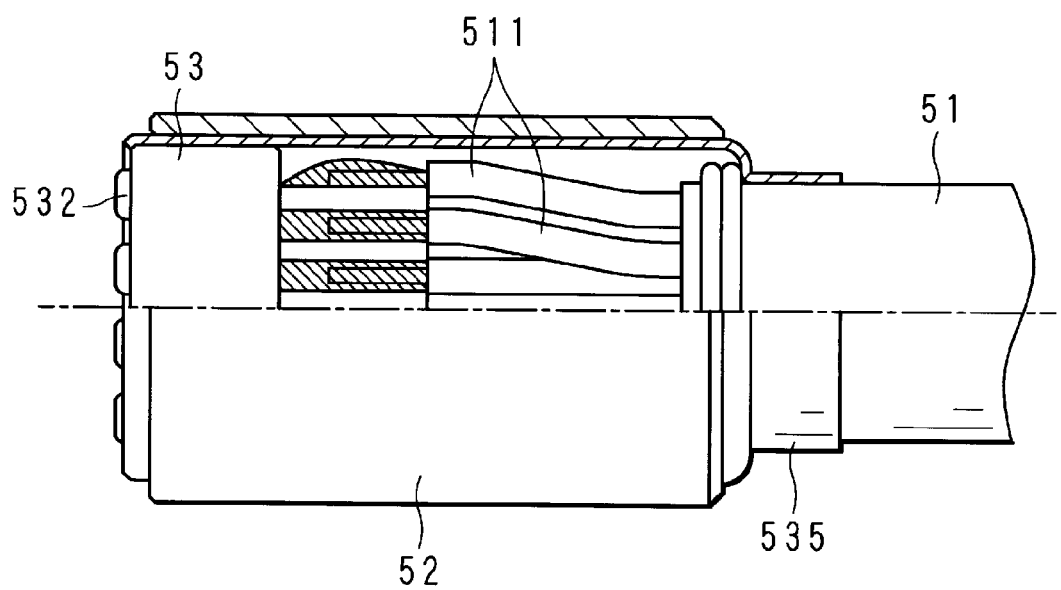
FIG. 12 is a partial half cross-sectional view of a cable assembly.
Figure 13:
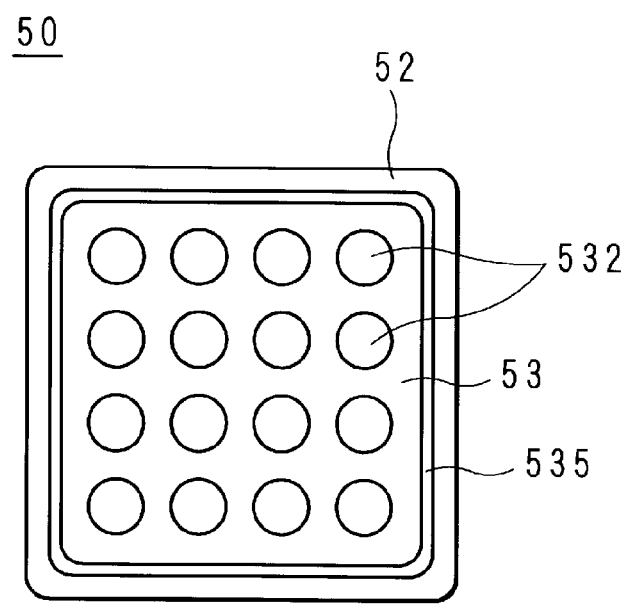
FIG. 13 is a side view of the cable assembly as viewed from a distal tip side.

FIG. 12 is a partial half cross-sectional view of the cable assembly 50. FIG. 13 is a side view of the cable assembly 50 as viewed from the distal tip side. In FIGS. 12 and 13, the left side is the distal tip side and the right side is the operation unit side. The cable assembly 50 includes the cable bundle 51, a connection block 53, and a connection frame 52.

As described above, the cable bundle 51 is a bundle of the plurality of cable strands 511 and is covered with an outer sheath. The individual cable strand 511 also has an insulating outer sheath. Note that the cable strand 511 used for signal transmission performed with the image sensor 611 is preferably a coaxial cable including a core wire, a dielectric layer, and a shield wire. The cable strand 511 may also be an optical fiber for optical communication.

The connection block 53 is a multilayer substrate formed in a prismatic shape or a square plate shape. As illustrated in FIG. 13, a plurality of connection terminals 532 are arranged on an end surface of the connection block 53 on the distal tip side. Each connection terminal 532 is a protrusion formed of a highly conductive material, such as solder or copper. The surface of the connection terminal 532 is preferably covered with an anticorrosion film such as gold or nickel.

Pins or terminals to which the cable strands 511 can be connected are provided on an end surface of the connection block 53 on the operation unit side. The connection terminals 532 and the pins or terminals are one-to-one conducted inside the connection block 53. The connection frame 52 is a square cylinder having an inner dimension slightly larger than that of the connection block 53. The connection frame 52 is formed of a high-strength material such as stainless steel.

The outer sheath of an end portion of the cable bundle 51 is removed to expose the cable strand 511. Conductors of the respective cable strands 511 are connected to the pins or terminals by soldering or the like. The connected portion is covered with an insulator such as a heat shrink tube to prevent the occurrence of a short circuit. A side surface of the connection block 53 and the connected portion are covered with an insulating tube 535 and the connection frame 52. The insulating tube 535 is a heat shrink tube longer than the connection frame 52.

The connected portion is potted with an insulating potting resin. The potting resin fills the inside of the insulating tube 535 and the connection frame 52. An end portion of the insulating tube 535 on the operation unit side shrinks to be in close contact with the outer sheath of the cable bundle 51.

As described above, an end portion of the cable assembly 50 on the distal tip side is formed in a substantially prismatic shape. Since the inside of the connection frame 52 is filled with the potting resin, troubles such as disconnection are prevented even when an external force is applied.

Figure 14:
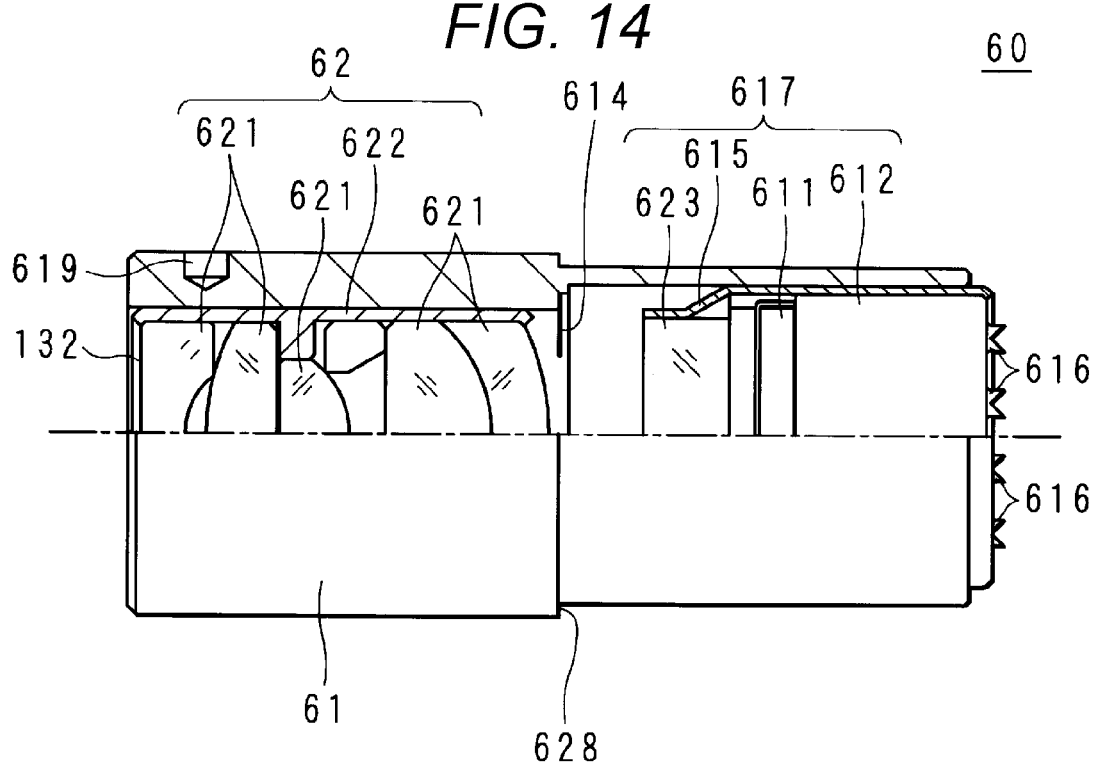
FIG. 14 is a half cross-sectional view of an imaging unit.

FIG. 14 is a half cross-sectional view of the imaging unit 60. In FIG. 14, the left side is the distal tip side and the right side is the operation unit side. The imaging unit 60 is a component in which the image sensor 611 and an optical component that forms an optical image on the image sensor 611 are assembled in focus. The imaging unit 60 includes an imaging frame 61, the image sensor 611, an imaging board 612, a filter 623, an imaging lens frame 622, an imaging lens 621, and a light-blocking mask 614.

The outer shape of the imaging frame 61 is substantially prismatic, and an outer dimension on the distal tip side is slightly larger than that on the operation unit side. A contact wall 628 substantially perpendicular to the longitudinal direction is formed at a boundary between the distal tip side and the operation unit side.

The operation unit side of the imaging frame 61 has a uniform thickness and a square cylinder shape. The distal tip side of the imaging frame 61 is thicker than the operation unit side of the imaging frame 61, and an inner surface has a cylindrical shape. Two claw holes 619 are symmetrically arranged in portions of a side surface that are near a distal tip of the imaging frame 61. The imaging frame 61 is formed of a high-strength material such as stainless steel.

The imaging board 612 is a component-embedded board formed in a prismatic shape or a square plate shape. In the imaging board 612, a driver circuit that controls the image sensor 611 is embedded. The image sensor 611 is mounted on a surface of the imaging board 612 on the distal tip side. A plurality of imaging terminals 616 are arranged on a surface of the imaging board 612 on the operation unit side.

The imaging terminal 616 has a plurality of claws that protrude toward the operation unit side. The imaging terminal 616 is formed by coating the surface of a conductor having a high hardness such as brass with gold plating. The arrangement of the imaging terminal 616 corresponds to the connection terminal 532 described with reference to FIG. 13. An input/output terminal of the image sensor 611 is connected to the imaging terminal 616 via the driver circuit inside the imaging board 612.

The filter 623 is attached to the distal tip side of the image sensor 611. The filter 623 removes unnecessary light such as infrared rays from light incident on the image sensor 611, and performs adjustment so that an image having a desired hue can be captured.

Side surfaces of the filter 623, the image sensor 611, and the imaging board 612 are covered with an insulating tube 615 to form an image sensor assembly 617. The insulating tube 615 is a heat shrink tube, and shrinks to be contact with the side surface of each component. It is preferable that the insulating tube 615 has a lightproof property in order to prevent stray light from being incident on the image sensor 611.

The imaging lens frame 622 fixes a plurality of imaging lenses 621 at appropriate positions to form the imaging lens assembly 62. The light-blocking mask 614 is fixed to an inner surface of the imaging lens frame 622. The light-blocking mask 614 prevents unnecessary peripheral light rays from being incident on the image sensor 611 from the imaging lens assembly 62.

The imaging unit 60 is manufactured by inserting the imaging lens assembly 62 and the image sensor assembly 617 into the imaging frame 61, performing focusing, and then firmly fixing the imaging lens assembly 62 and the image sensor assembly 617 with an adhesive or the like. The imaging unit 60 includes expensive components such as the image sensor 611 and the imaging lens 621, and thus is an expensive component that requires focusing. In the present embodiment, the imaging unit 60 is collected from the used endoscope 10 and reused for manufacturing a new endoscope 10.

Figure 15:
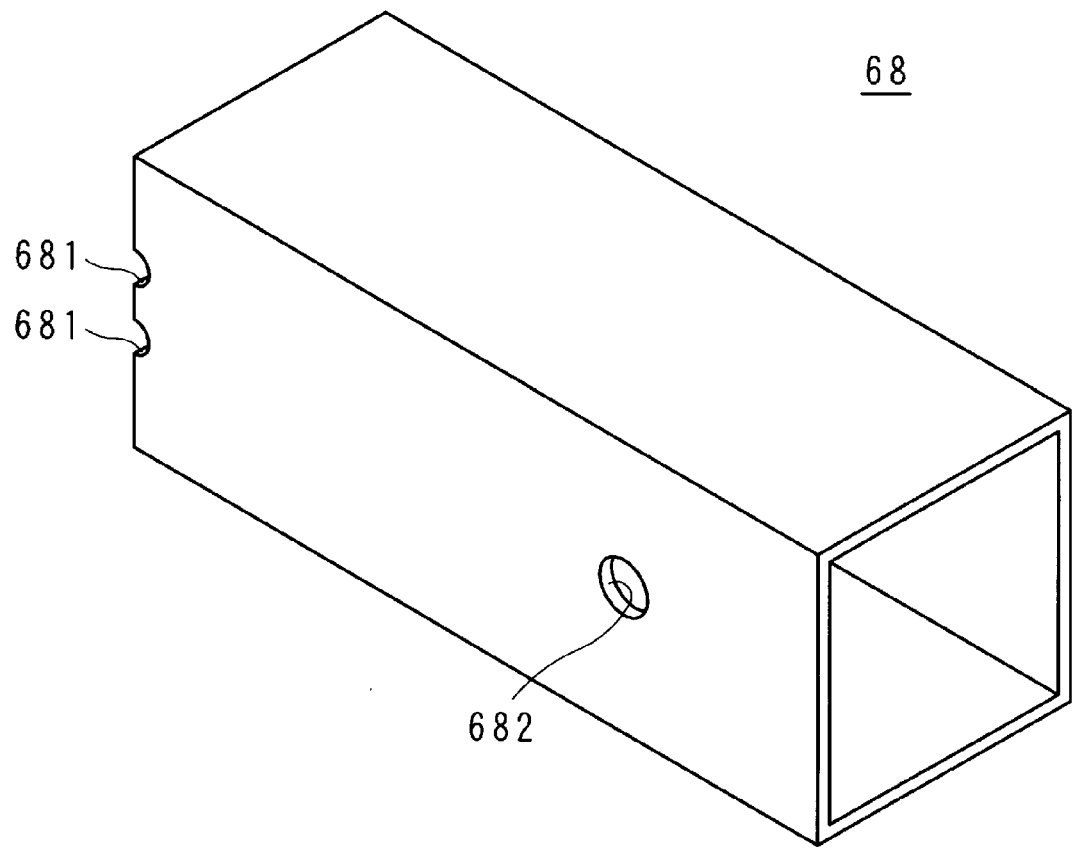
FIG. 15 is a perspective view of an exterior cylinder.

FIG. 15 is a perspective view of the exterior cylinder 68. In FIG. 15, the left side is the distal tip side and the right side is the operation unit side. The exterior cylinder 68 is a connecting member that connects the cable assembly 50 and the imaging unit 60. The exterior cylinder 68 has a thin-walled square cylinder shape. Two semi-circular cylinder notches 681 are provided side by side at one end portion of one surface of the exterior cylinder 68, and a holding recess

682 which is a round hole is provided near an end portion that is opposite to the one end.

The exterior cylinder 68 is manufactured by cutting and drilling a square pipe formed of a material that is more easily broken as compared with the imaging frame 61, such as brass or a resin. The exterior cylinder 68 may be manufactured by bending a thin plate formed of brass, a resin, or the like. In a case of using brass, the wall thickness of the exterior cylinder 68 is preferably about 0.1 mm to 0.2 mm.

The exterior cylinder 68 may have a shape in which a through-hole having a shape corresponding to the outer diameter shape of the imaging frame 61 and the connection frame 52 is formed in a bar material having an arbitrary shape, such as a round bar or a square bar.

An outline of a method of manufacturing the imaging/cable unit 15 will be described with reference to FIGS. 11 to 15. An adhesive is applied to the side surface of the imaging frame 61 on the operation unit side. The exterior cylinder 68 is put on so that the exterior cylinder 68 abuts on the contact wall 628. The adhesive is sufficiently cured. As described above, the imaging unit 60 and the exterior cylinder 68 are fixed.

The adhesive is applied to the side surface of the connection frame 52. The portion coated with the adhesive is inserted into the exterior cylinder 68, such that the connection terminal 532 and the imaging terminal 616 are abutted on each other. The connection terminal 532 is pushed toward the imaging terminal 616 by caulking an edge of the connection frame 52 on the operation unit side to form an inwardly bent portion 685.

Figure 16:
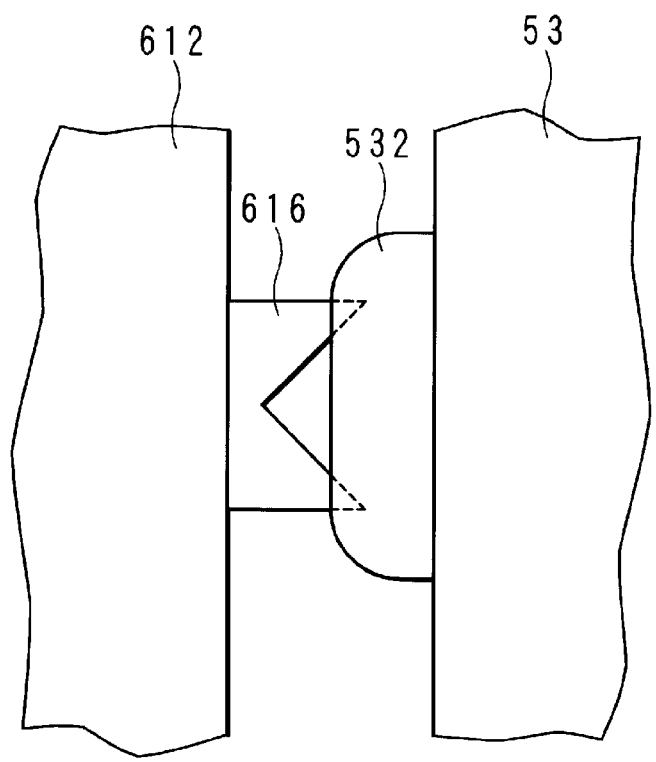
FIG. 16 is an enlarged view of Part A in FIG. 11.

FIG. 16 is an enlarged view of Part A in FIG. 11. A distal tip of the imaging terminal 616 pierces the connection terminal 532, such that a strong connection state can be achieved. The adhesive is sufficiently cured. As described above, the imaging unit 60 and the cable assembly 50 are fixed in a connected state, and the imaging/cable unit 15 is completed.

As described above, the connection terminal 532 is formed of a highly conductive material such as solder or copper, and the imaging terminal 616 is formed of a conductor material having a high hardness, such as brass. Since the material of the imaging terminal 616 has a higher hardness than that of the material of the connection terminal 532, the imaging terminal 616 pierces the connection terminal with almost no damage such as deformation or scratch. Therefore, the imaging unit 60 can be used repeatedly.

Figure 17:
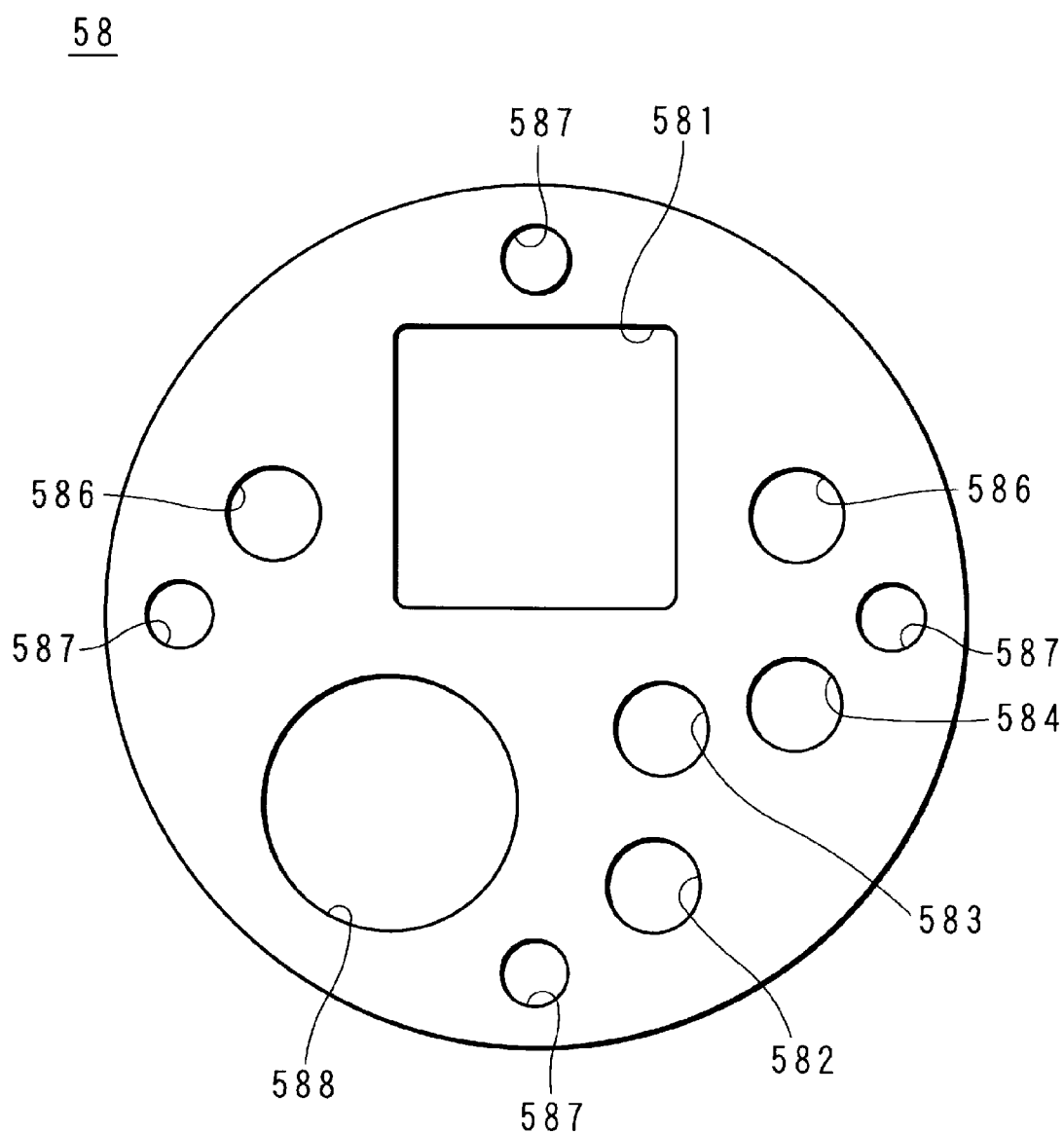
FIG. 17 is a front view of an abutting plate.

FIG. 17 is a front view of the abutting plate 58. The abutting plate 58 is a disk formed of a high-strength material such as stainless steel. The abutting plate 58 has a square hole 581, a jet hole 582, an air supply hole 583, a water supply hole 584, an illumination hole 586, a wire hole 587, and a channel hole 588. All of them are through-holes. Since the arrangement of each hole is the same as the layout of the distal tip piece 13 described with reference to FIG. 10, the description thereof will be omitted.

As described above, the wire hole 587 has a dimension in which the bending wire 17 can be inserted, but the bending wire stopper 171 cannot be inserted.

Figure 18:
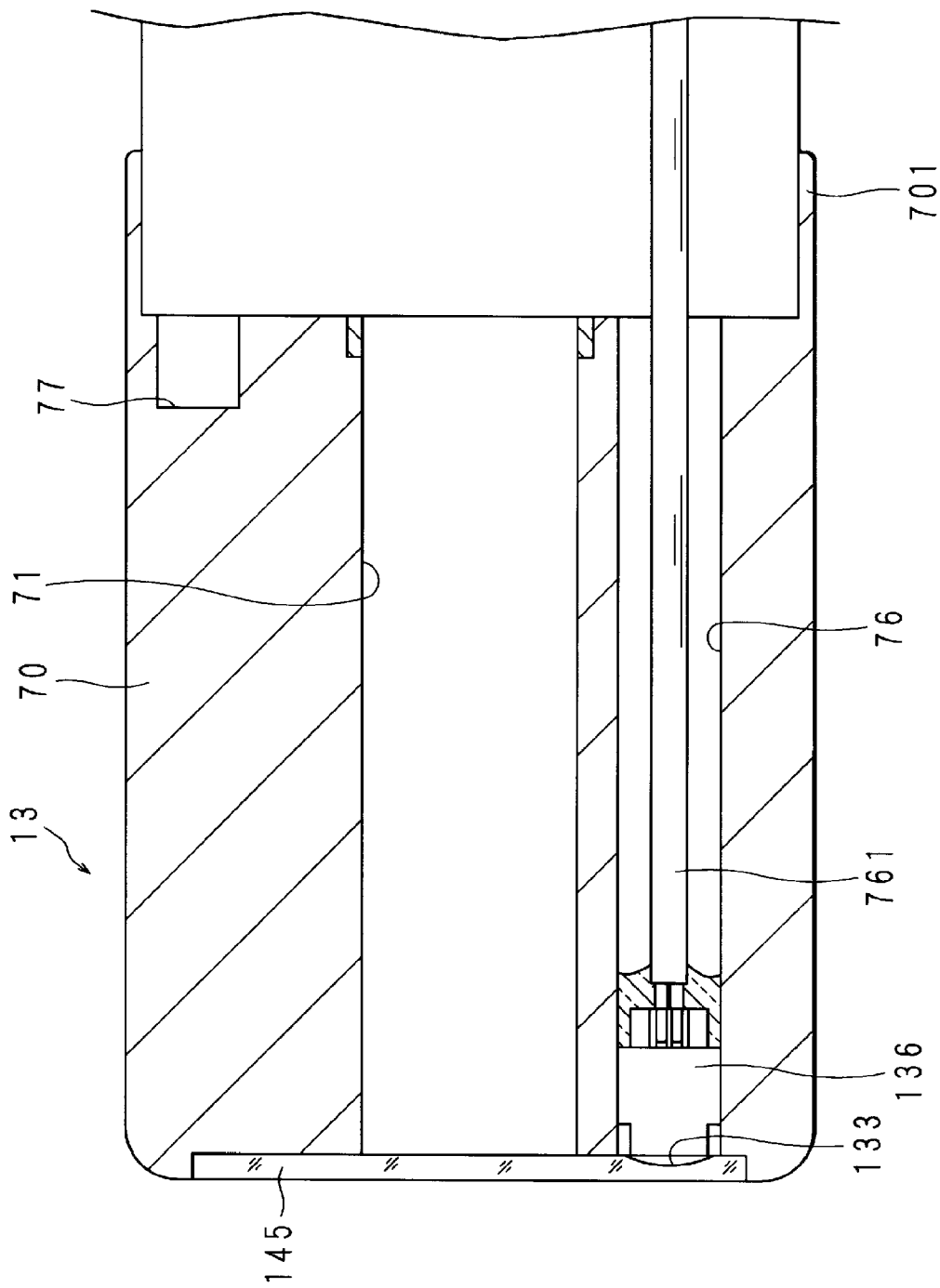
FIG. 18 is an explanatory view for describing a method of assembling the endoscope.
Figure 19:
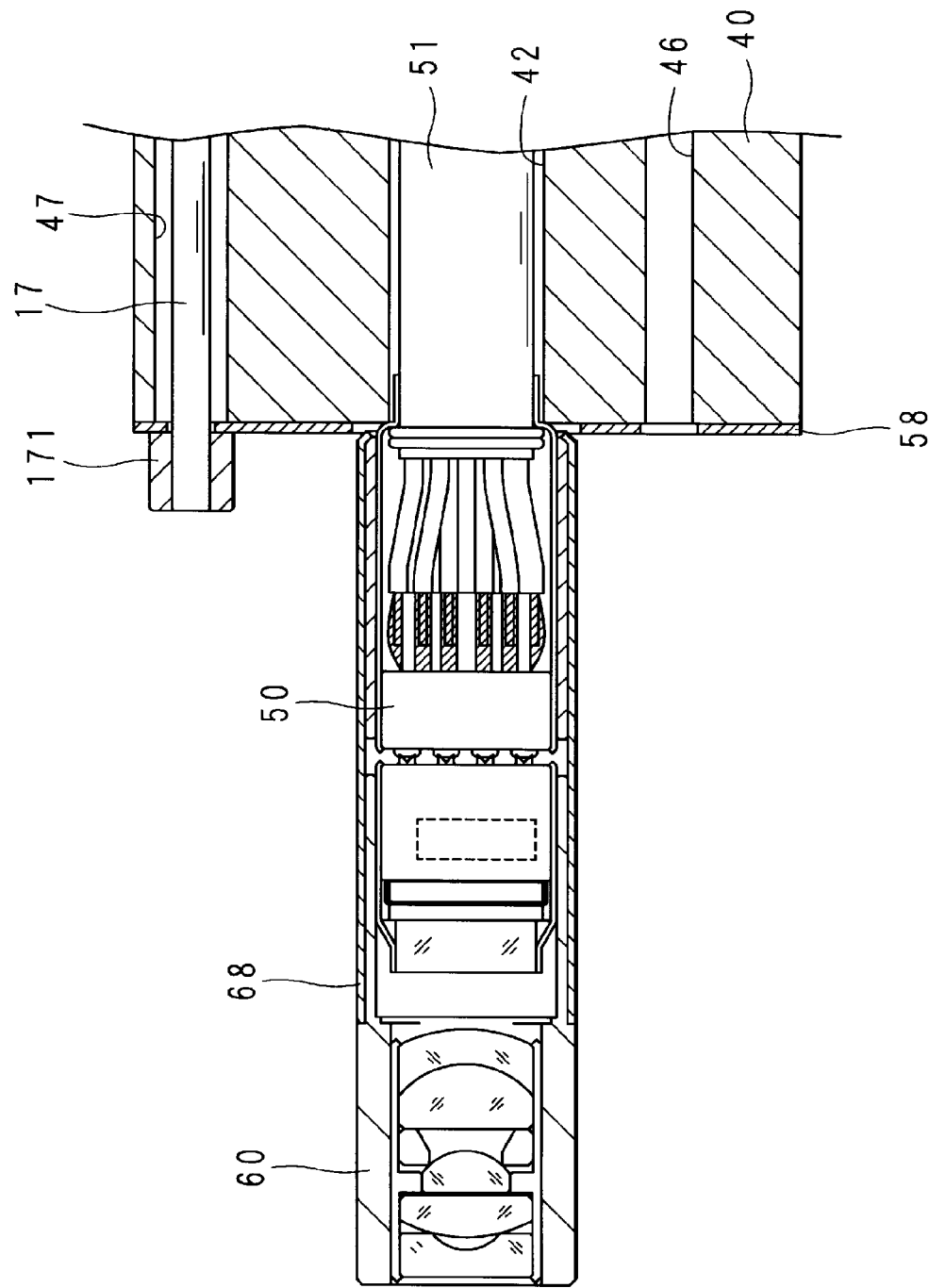
FIG. 19 is an explanatory view for describing the method of assembling the endoscope.

FIGS. 18 and 19 are explanatory views for describing a method of assembling the endoscope 10. Note that a method of assembling the insertion portion 14 will be described below, and a description of the assembly of the operation unit 20 and the connector unit 24 will be omitted.

FIGS. 18 and 19 are cross-sectional views illustrating the same cross section as in FIG. 6. As illustrated in FIG. 18, the light emitting element 136 connected to the illumination cable 761 is inserted into and bonded to each of two illumination holes 76.

As illustrated in FIG. 19, the bending wire 17 is inserted into the bending wire hole 47 and the cable bundle 51 is inserted into the cable hole 42 in a state where the abutting plate 58 abuts on the end surface of the unused multi-lumen tube 40.

The adhesive is applied to an inner surface of the distal tip frame edge 701 and the outer surface of each pipe. The illumination cable 761 is inserted into the illumination hole 46. A prismatic portion of the imaging/cable unit frame 151 enters the square hole 71, and the bending wire stopper 171 enters the wire stopper hole 77. The square hole 71 is an example of a housing portion of the present embodiment, which is fitted with the exterior cylinder 68 which is an exterior component of the prismatic portion. Note that a gap may be provided between the square hole 71 and the exterior cylinder 68.

Since the air hole 711 is provided, air between the distal tip of the imaging/cable unit 15 and the window plate 145 flows out to the outside. The channel pipe 781, the jet pipe 721, the air supply pipe 731, and the water supply pipe 741 also enter the corresponding holes provided in the multi-lumen tube 40, respectively.

The adhesive is cured in a state where the distal tip piece 13 and the end surface of the multi-lumen tube 40 abut on each other. The assembly of the operation unit 20 and the connector unit 24 is performed. As a result, the endoscope 10 described with reference to FIGS. 1 to 8 is completed. The endoscope 10 is packed in a sterilization pack, sterilized by, for example, electron beam sterilization, and then shipped.

The user uses the endoscope 10 only once. The used endoscope 10 is collected by the manufacturer, and infection prevention measures such as cleaning and sterilization are performed. Thereafter, the endoscope 10 is disassembled, and a reusable component such as the imaging unit 60 is collected. A predetermined inspection is performed on the reusable component, and in a case where the reusable component passes the inspection, the reusable component is used for manufacturing a new endoscope 10.

FIGS. 20 to 23 are explanatory views illustrating a method of disassembling the endoscope 10. FIGS. 20 to 23 are cross-sectional views illustrating the same cross section as in FIG. 3. First, the operation unit 20 is disassembled, and the connected portion of the cable bundle 51 on the operation unit side is removed.

The window plate 145 is removed from the distal tip frame 70. This work is carried out, for example, by inserting a jig into the gap between the edge of the window plate 145 and the edge of the window plate frame 75 described with reference to FIG. 2, and picking the gap.

The window plate 145 may be made removable by using an adhesive having a high temperature dependence, that is, an adhesive whose adhesive strength changes when the temperature changes, for bonding the window plate 145 to the distal tip frame 70. Specifically, an adhesive that rapidly deteriorates at a temperature which does not occur under normal transportation, storage and use conditions of the endoscope 10 and at which the imaging unit 60 does not deteriorate, for example, a temperature of about 60 to 70 degrees, is used for the bonding between the window plate 145 and the distal tip frame 70. For example, an adhesive having a glass transition point of about 60 to 70 degrees is used, or a hot melt adhesive having a softening point of about 60 to 70 degrees is used. In this case, the window plate 145 can be removed by warming the endoscope 10 to the temperature.

Figure 20:
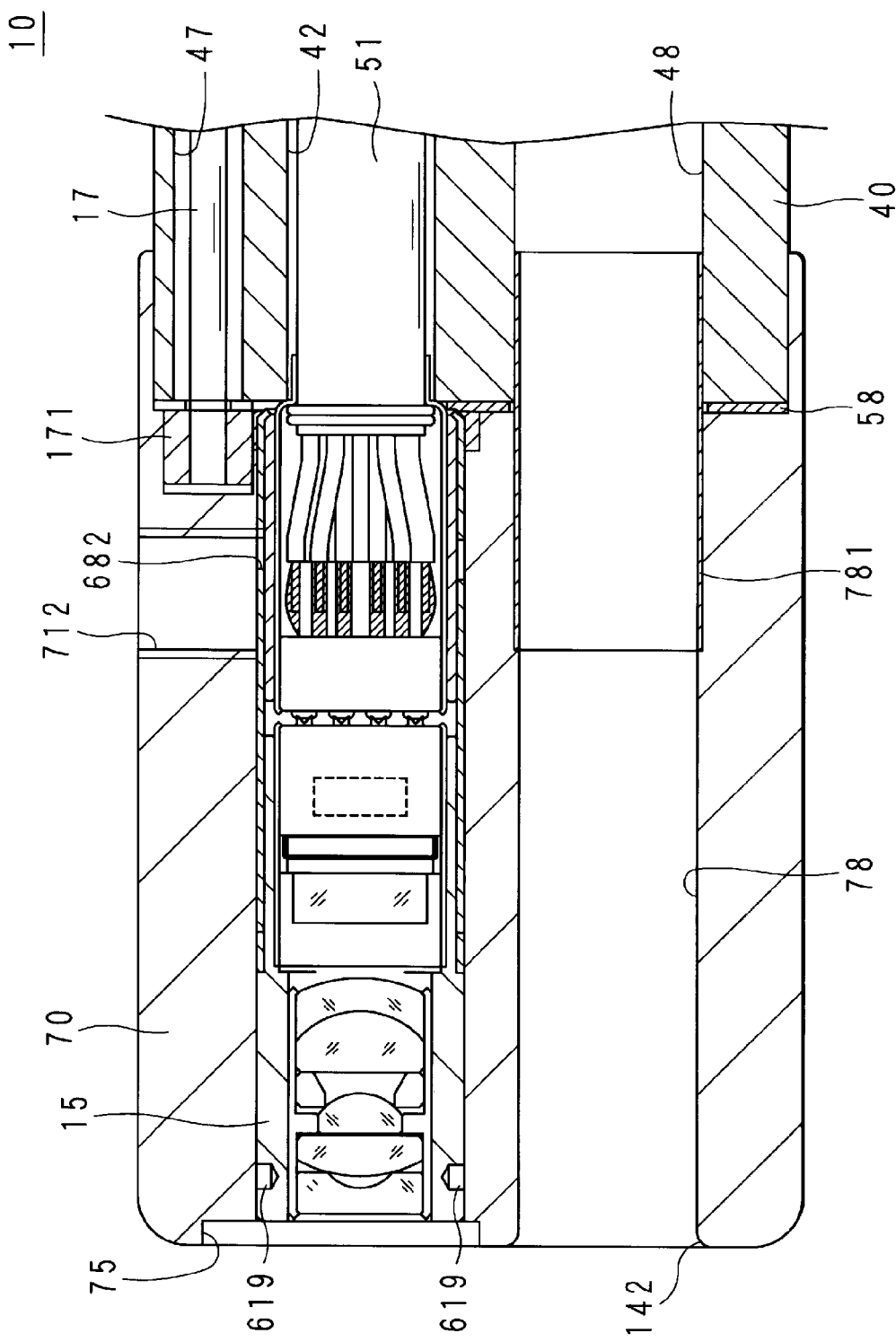
FIG. 20 is an explanatory diagram for describing a method of disassembling the endoscope.

The adhesive covering the head portion of the fixing screw 69 is removed with a tweezer or the like. Then, the fixing screw 69 and the protection sheet 691 are removed. As a result, the state illustrated in FIG. 20 is realized. The holding recess 682 is exposed inside the communication hole 712 on the operation unit side.

Figure 21:
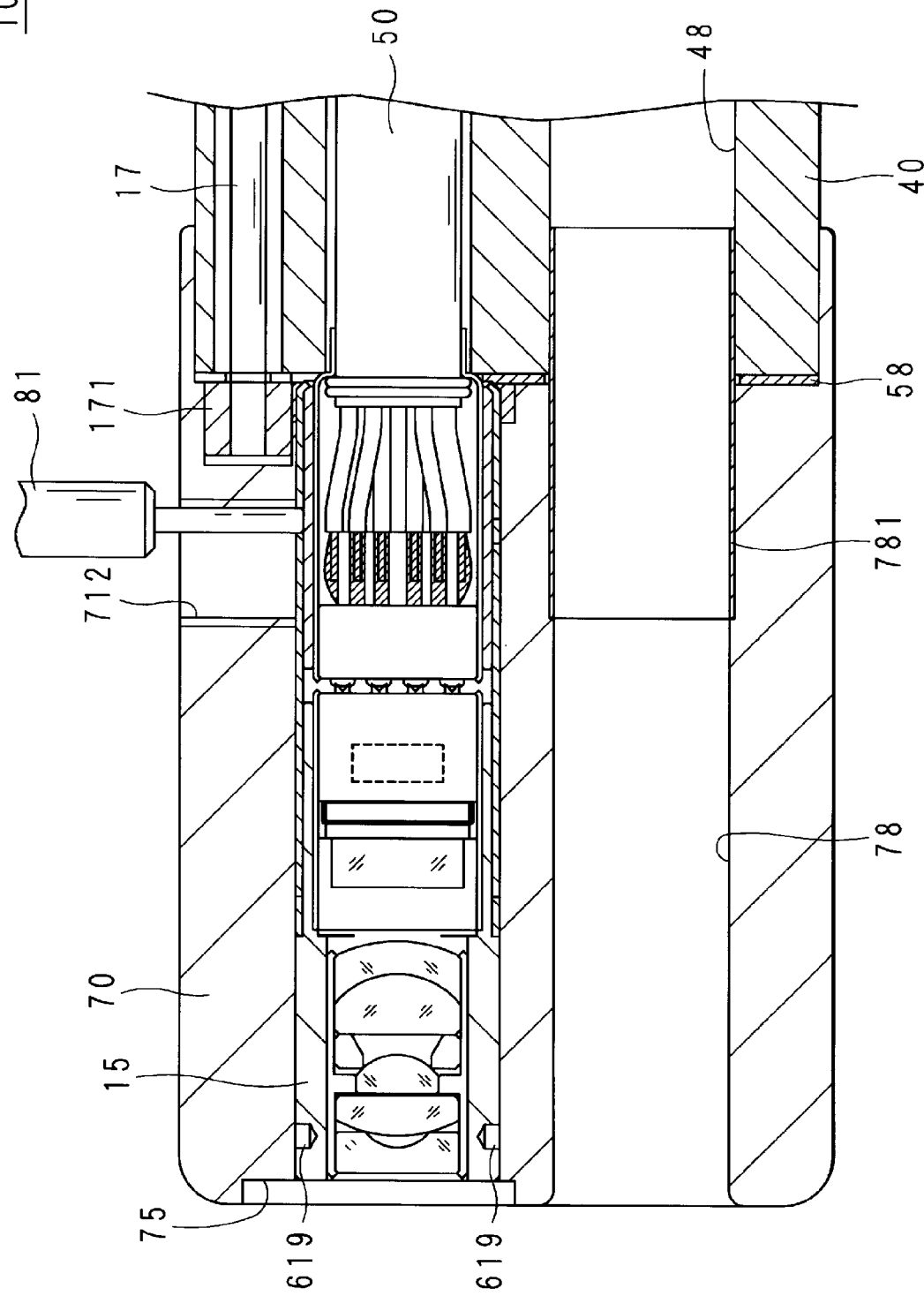
FIG. 21 is an explanatory view for describing the method of disassembling the endoscope.
Figure 22:
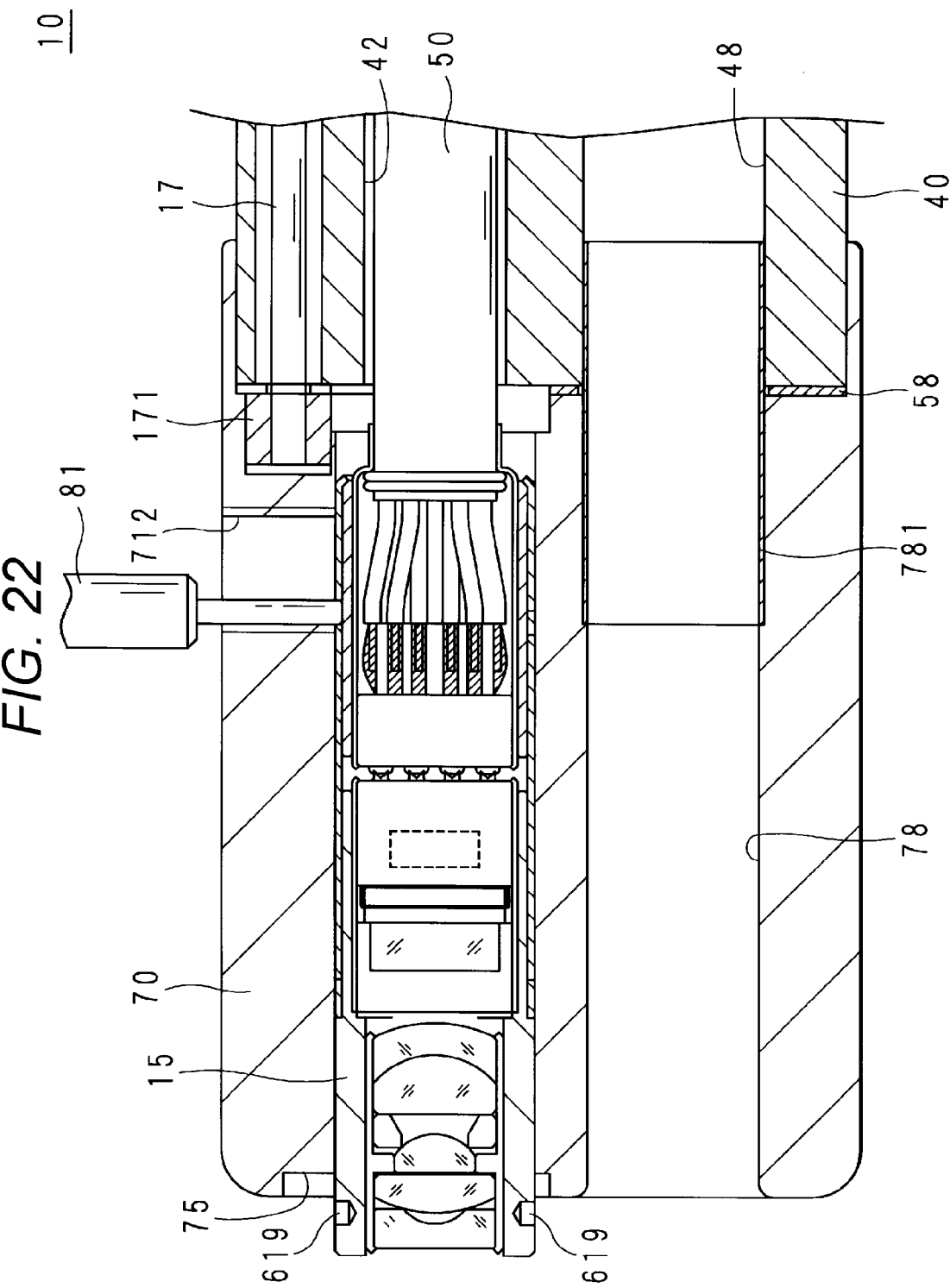
FIG. 22 is an explanatory view for describing the method of disassembling the endoscope.

The description will be continued with reference to FIG. 21. An extrusion jig 81 having a bar-shaped distal tip is inserted into the holding recess 682 through the communication hole 712. By pushing the holding recess 682 toward the distal tip side using the extrusion jig 81, the distal tip of the imaging/cable unit 15 protrudes from the distal tip piece 13 as illustrated in FIG. 22.

Figure 23:
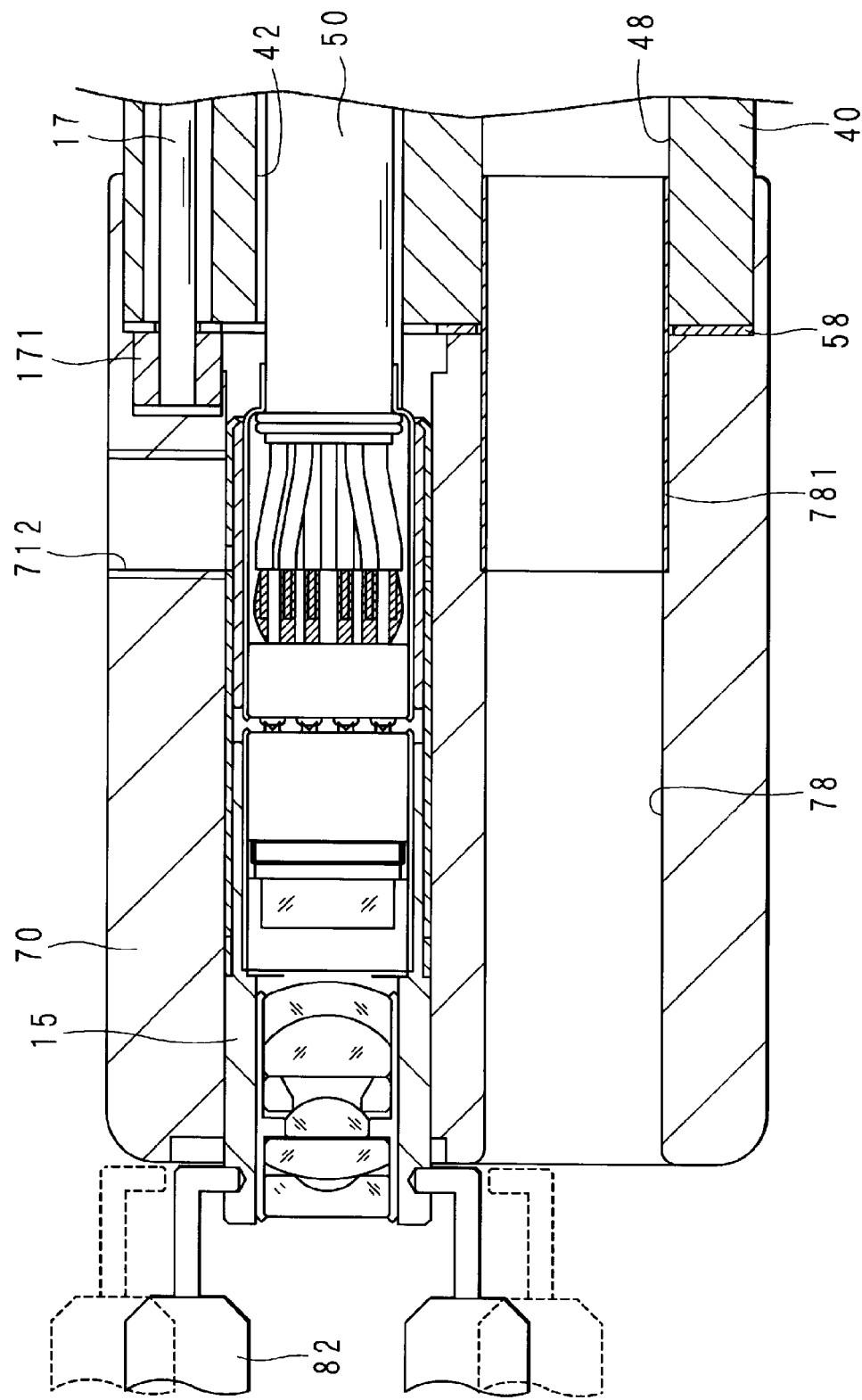
FIG. 23 is an explanatory view for describing the method of disassembling the endoscope.

The description will be continued with reference to FIG. 23. A claw jig 82 is inserted into two claw holes 619. The claw jig 82 is a jig in which pins corresponding to the claw holes 619 are fixed inward at opposite ends of a tool having a pinching function such as a tweezer or needle-nose plier. The imaging/cable unit 15 can be taken out from the endoscope 10 by pulling the claw jig 82.

The exterior cylinder 68 is removed from the taken-out imaging/cable unit 15. For example, a tool such as a tweezer is inserted into the cylinder notch 681 to tear the exterior cylinder 68. The ridgeline of the exterior cylinder 68 may be scraped off with a file. Since the imaging frame 61 and the connection frame 52 are formed of a material having a higher strength than that of the exterior cylinder 68, it is possible to destroy only the exterior cylinder 68.

Similarly to the process of removing the window plate 145 described above, the exterior cylinder 68 may be removed by using an adhesive having a high temperature dependence at the time of assembly and warming the imaging/cable unit 15. By removing the exterior cylinder 68 by some means, the imaging unit 60 can be collected without being destroyed.

The collected imaging unit 60 is subjected to a predetermined quality inspection, and in a case where the collected imaging unit 60 passes the inspection, the collected imaging unit 60 is reused for manufacturing a new endoscope 10.

According to the present embodiment, it is possible to provide an endoscope 10 in which the imaging unit 60 can be reused. By reusing expensive components, a high-definition single-use endoscope 10 can be provided at low cost.

The imaging unit 60 can be commonly used for endoscopes 10 having different specifications such as a channel diameter or an effective length. Therefore, an endoscope 10 that meets the needs of the user can be promptly provided.

For example, a component other than the imaging unit 60, such as the abutting plate 58, may be reused. In a case where the imaging/cable unit 15 can be taken out from the endoscope 10 without damaging the cable assembly 50, the entire imaging/cable unit 15 may be reused without destroying the exterior cylinder 68.

Note that the distal tip piece 13 does not have to include some or all of the channel pipe 781, the jet pipe 721, the air supply pipe 731, and the water supply pipe 741. In this case, a pipe that is not included in the distal tip piece 13 is attached to the distal tip of the multi-lumen tube 40.

[Second Embodiment]

The present embodiment relates to an endoscope 10 in which a cable assembly 50 and an imaging unit 60 are integrally formed. Descriptions regarding the same part as those of the first embodiment will be omitted.

Figure 24:
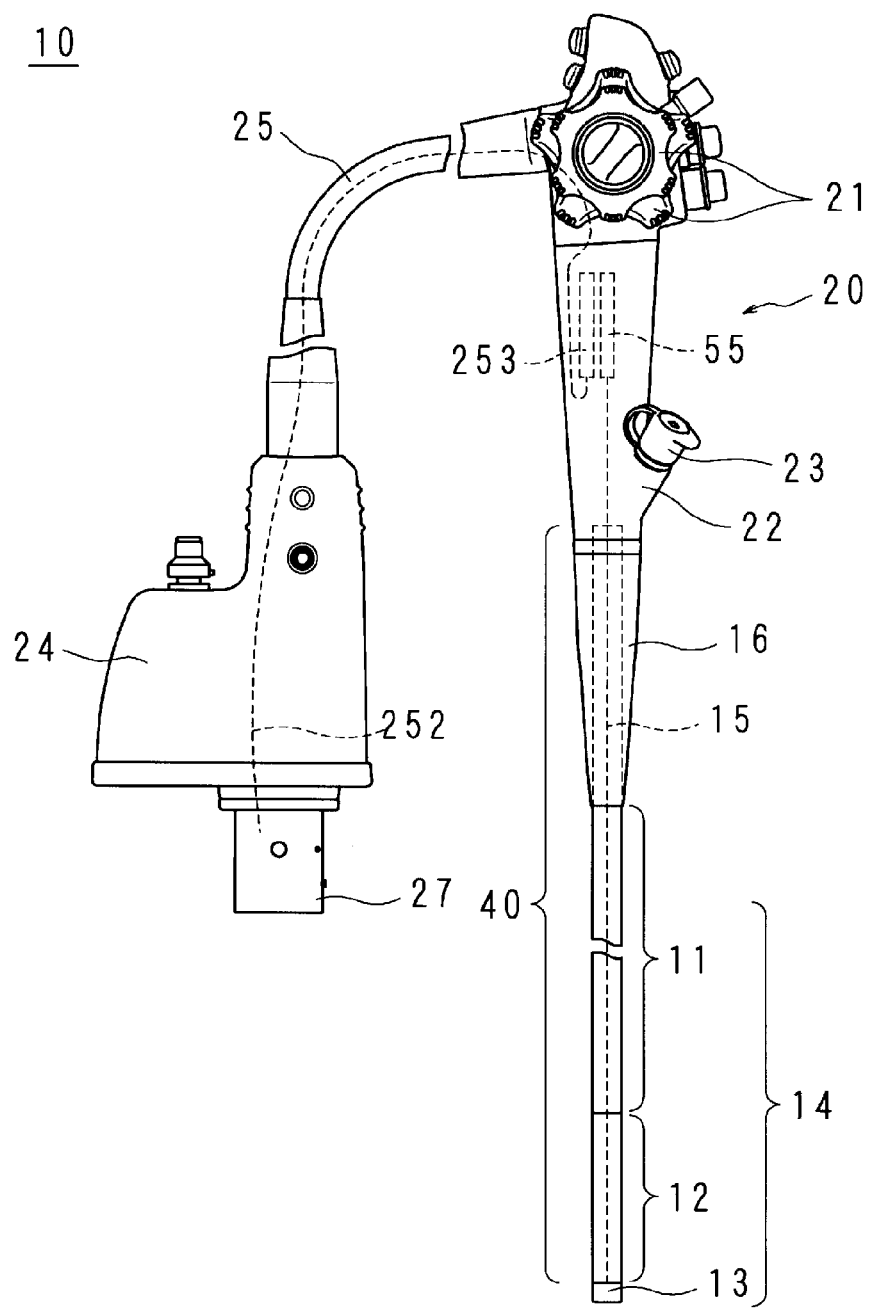
FIG. 24 is an explanatory diagram for describing an endoscope of a second embodiment.

FIG. 24 is an explanatory diagram for describing an endoscope 10 of the second embodiment. A first relay board 55 is provided at an end portion of an imaging/cable unit 15 on the operation unit side. Details of the configuration of the first relay board 55 will be described later. A second cable assembly 252 extends from a scope connector 27 to the inside of an operation unit 20 via a universal cord 25. A second relay board 253 is provided at an end portion of the second cable assembly 252.

Figure 25:
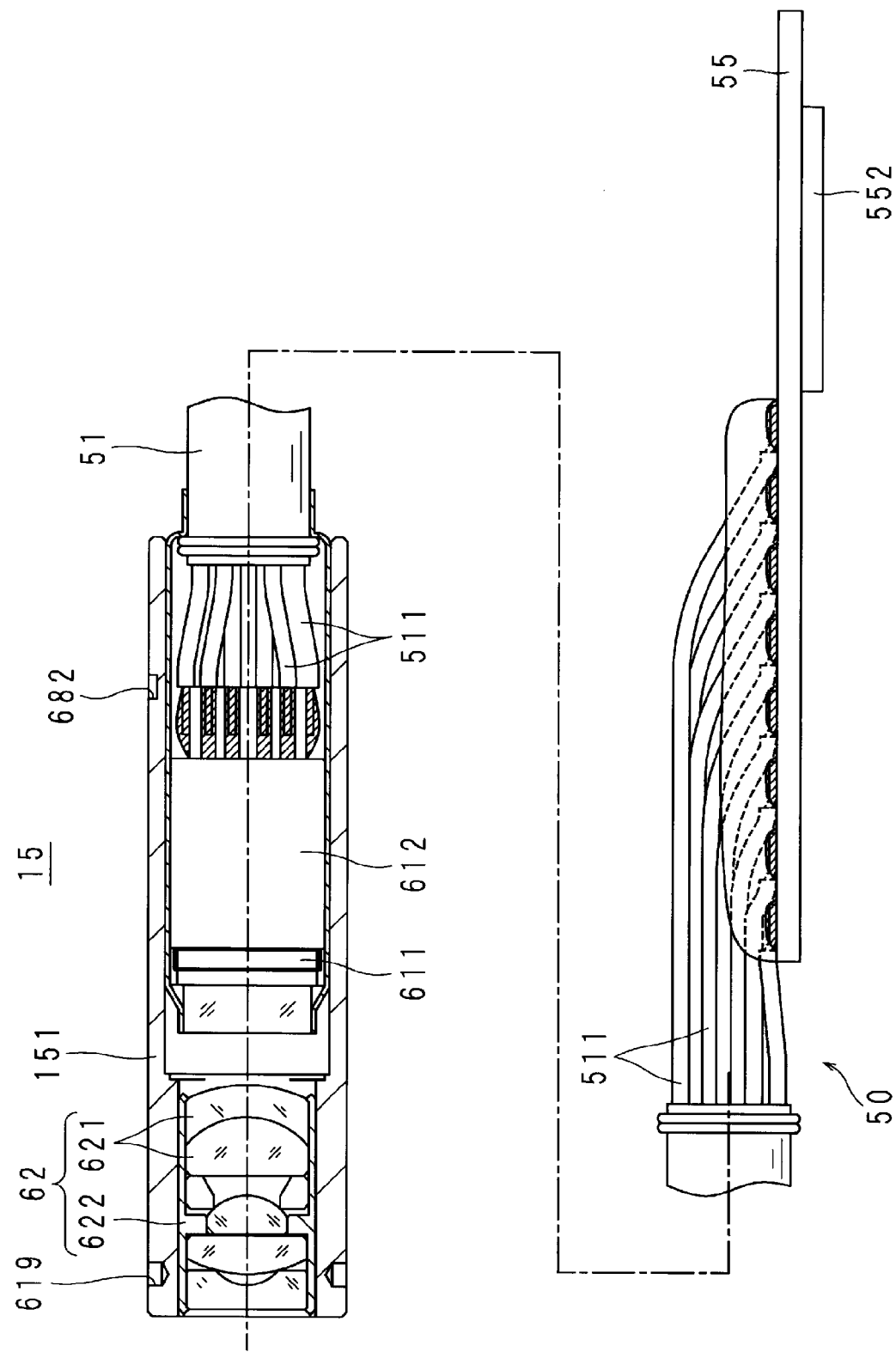
FIG. 25 is a partial cross-sectional view of an imaging/cable unit of the second embodiment.

FIG. 25 is a partial cross-sectional view of the imaging/cable unit 15 of the second embodiment. The imaging/cable unit 15 of the present embodiment includes an imaging lens assembly 62, the cable assembly 50, and an imaging/cable unit frame 151.

An outer shape of the imaging/cable unit frame 151 is prismatic, and a cylindrical hole is provided on the distal tip side and a prismatic hole is provided on the operation unit side. The imaging/cable unit frame 151 is formed of a high-strength material such as stainless steel. A set of claw holes 619 is provided in portions of an outer surface of the imaging/cable unit frame 151 on the distal tip side. A holding recess 682 is provided in a portion of the outer surface of the imaging/cable unit frame 151 on the operation unit side.

The cable assembly 50 has a configuration in which a cable strand 511 is connected to an imaging board 612 on which an image sensor 611 is mounted. The imaging lens assembly 62 and the cable assembly 50 are fixed to the inside of the imaging/cable unit frame 151 in a state where focusing is performed.

Figure 26:
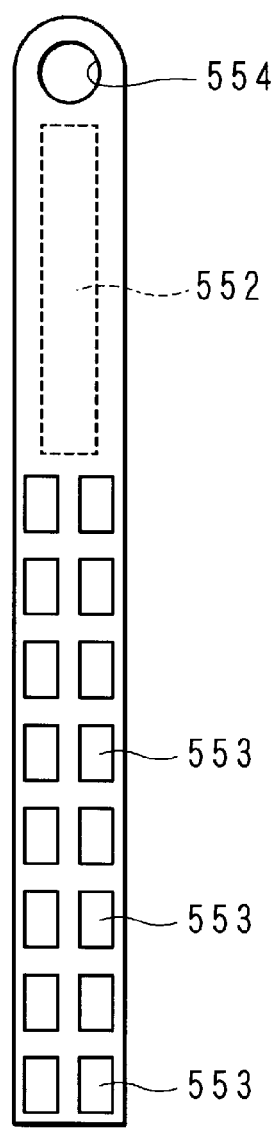
FIG. 26 is a front view of a first relay board.

FIG. 26 is a front view of the first relay board 55. The first relay board 55 is a long plate-shaped multilayer board, and has an attaching hole 554 formed at one end thereof. Lands 553 are arranged on one surface of the first relay board 55. A board-to-board connector 552, which is a board-to-board connector, is mounted on the other surface. The land 553 and a terminal of the board-to-board connector 552 are connected inside the first relay board 55.

Returning to FIG. 25, the description will be continued. End portions of the respective cable strands 511 included in the cable assembly 50 on the operation unit side are soldered to the lands 553, respectively. The soldered portion is covered with a potting resin.

Figure 27:
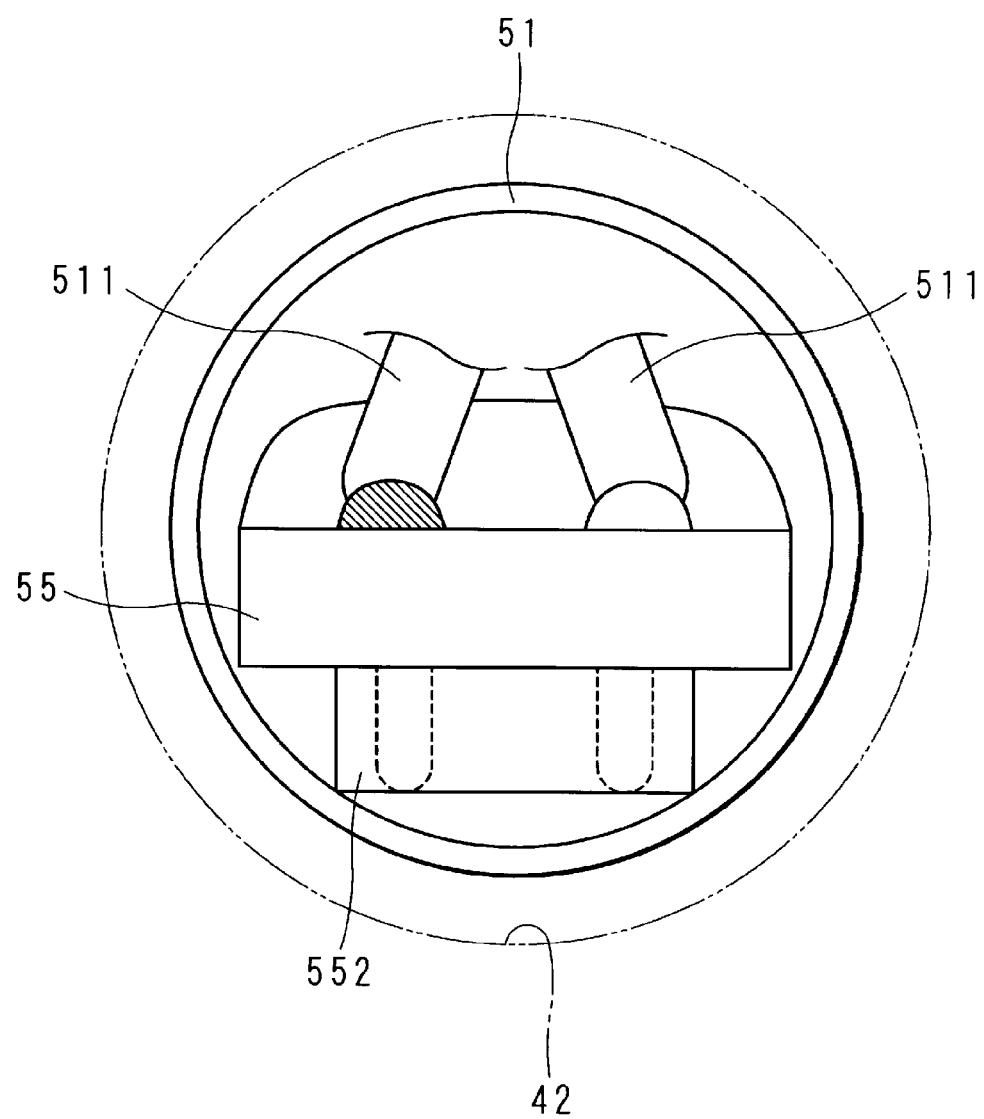
FIG. 27 is an explanatory view for describing the size of the first relay board.

FIG. 27 is an explanatory view for describing the size of the first relay board 55. A circle of a line with alternating long and short dashes indicates the inner diameter of a cable hole 42 penetrating a multi-lumen tube 40. The first relay board 55, the board-to-board connector 552, the cable strand 511, and the potting resin are mounted so that the sizes thereof are smaller than the outer diameter of the cable bundle 51. Therefore, the first relay board 55 of the present embodiment can pass through the cable hole 42, and can be removed from the endoscope 10 and reused without destroying the imaging/cable unit 15.

Figure 28:
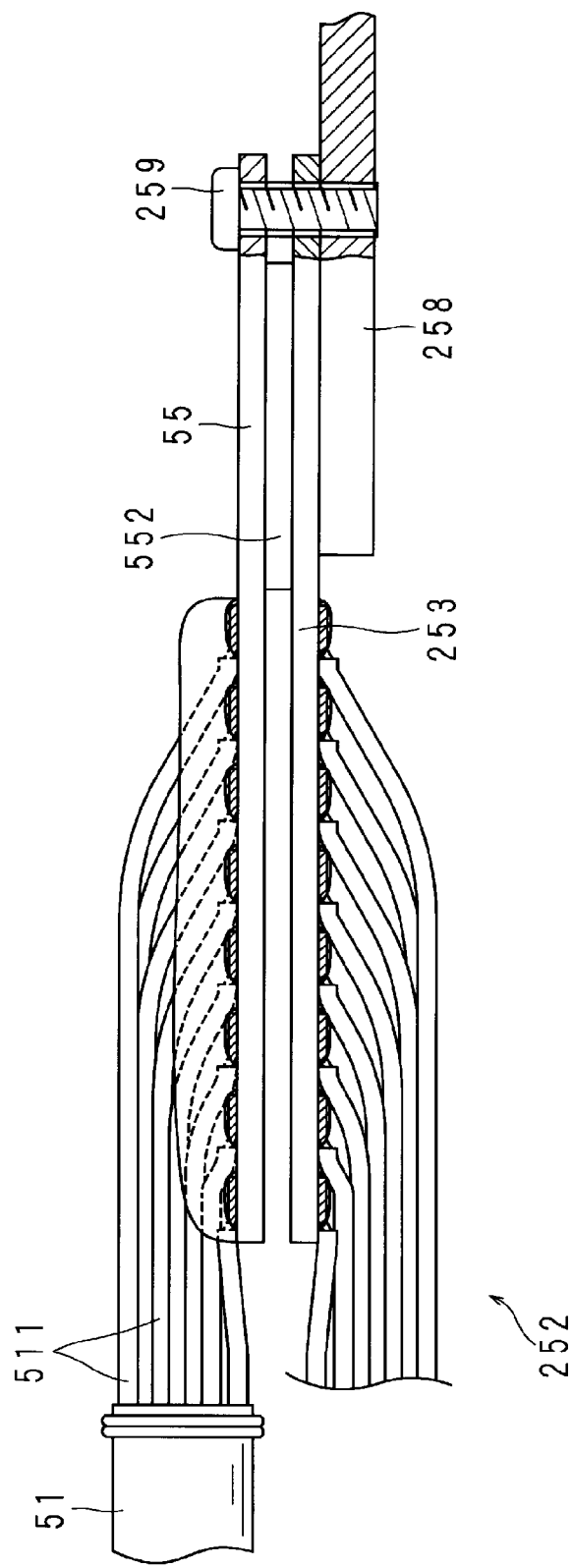
FIG. 28 is an explanatory view for describing a method of connecting the imaging/cable unit and a second cable assembly.

FIG. 28 is an explanatory view for describing a method of connecting the imaging/cable unit 15 and the second cable assembly 252. The board-to-board connector 552 mounted on the first relay board 55 and a connector provided on the second relay board 253 are fitted together. The imaging/cable unit 15 and the second cable assembly 252 are screwed to a frame 258 attached inside the operation unit 20 by using an attaching screw 259 penetrating the attaching hole 554 and a through-hole provided in the second relay board 253.

According to the present embodiment, a reusable endoscope 10 can be provided by removing the imaging/cable unit 15 without breaking the cable bundle 51. Similarly, the second cable assembly 252 may be removed from the universal cord 25 and reused.

[Third Embodiment]

The present embodiment relates to an endoscope 10 in which an exterior cylinder 68 and an imaging frame 61 are fixed by a pin. Descriptions regarding the same part as those of the first embodiment will be omitted.

Figure 29:
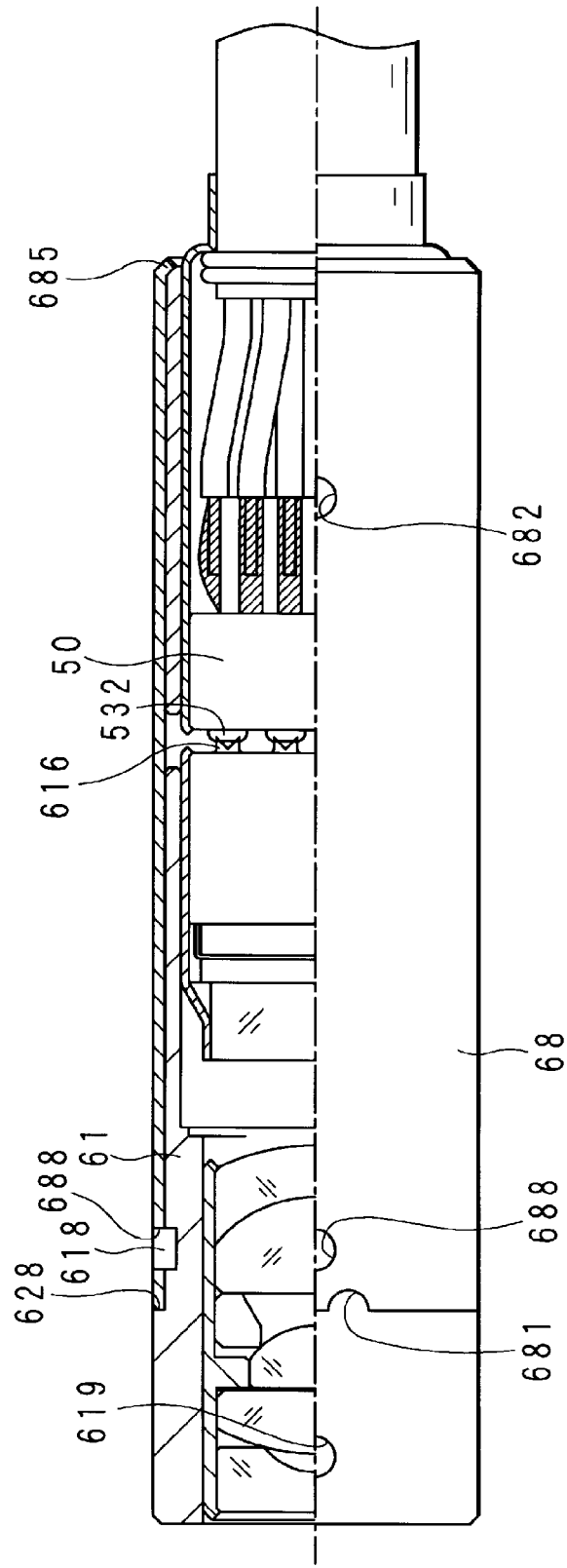
FIG. 29 is a half cross-sectional view of an imaging/cable unit of a third embodiment.
Figure 30:
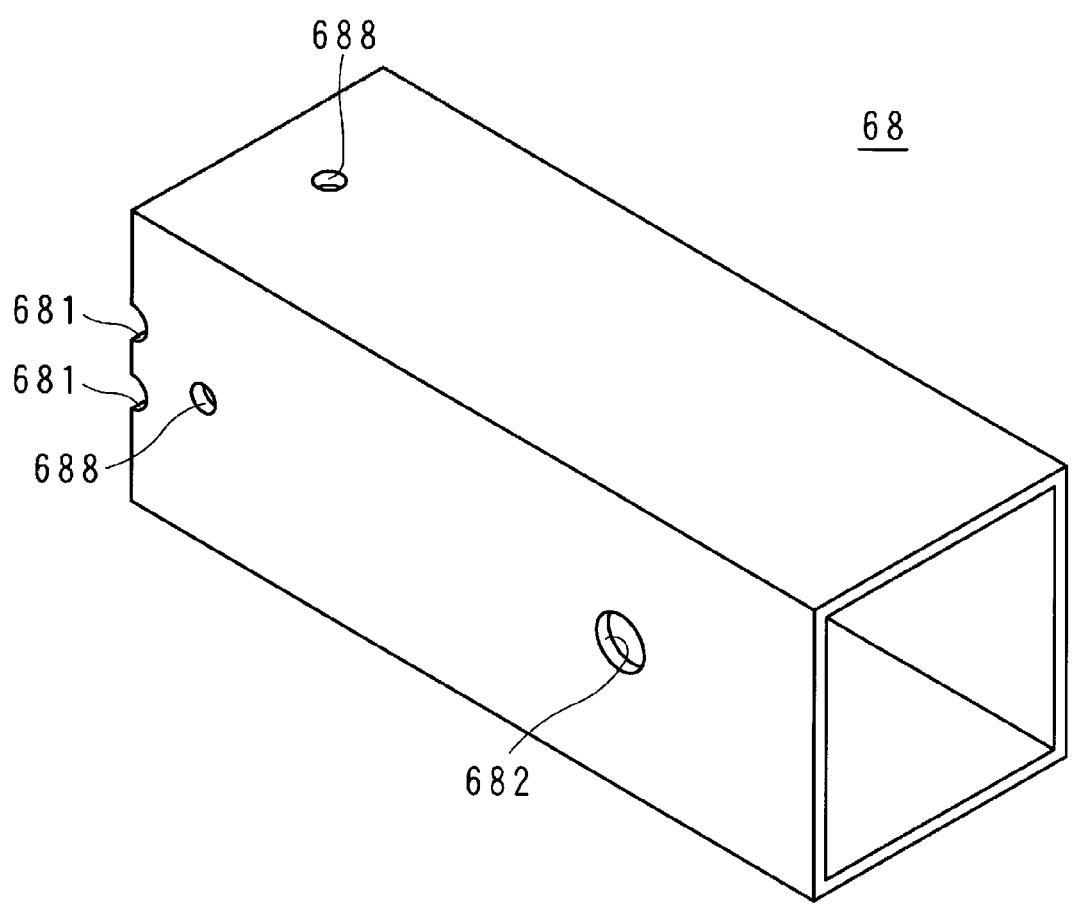
FIG. 30 is a perspective view of an exterior cylinder of the third embodiment.

FIG. 29 is a half cross-sectional view of an imaging/cable unit 15 of the third embodiment. FIG. 30 is a perspective view of the exterior cylinder 68 of the third embodiment. The imaging frame 61 of the present embodiment includes a contact wall 628 provided on an outer surface of a portion whose inner surface is cylindrical. A stopper protrusion 618 is provided upright in a portion of each surface of the imaging frame 61 that faces the operation unit side of the contact wall 628.

The exterior cylinder 68 has a stopper hole 688 formed in each surface thereof. As illustrated in FIG. 29, the stopper hole 688 and the stopper protrusion 618 are engaged with each other.

According to the present embodiment, an adhesive whose adhesive strength is relatively weak can be used for bonding between the imaging frame 61 and the exterior cylinder 68. The bonding between the imaging frame 61 and the exterior cylinder 68 may be omitted. Therefore, it is possible to provide an endoscope 10 in which an imaging unit 60 can be easily removed for reuse.

Note that the stopper protrusion 618 may be provided only on two surfaces parallel to each other. A plurality of stopper protrusions 618 may be provided on one surface.

[Fourth Embodiment]

The present embodiment relates to an endoscope 10 that uses an anisotropic conductive film for connecting an imaging terminal 616 and a connection terminal 532. Descriptions regarding the same part as those of the first embodiment will be omitted.

Figure 31:
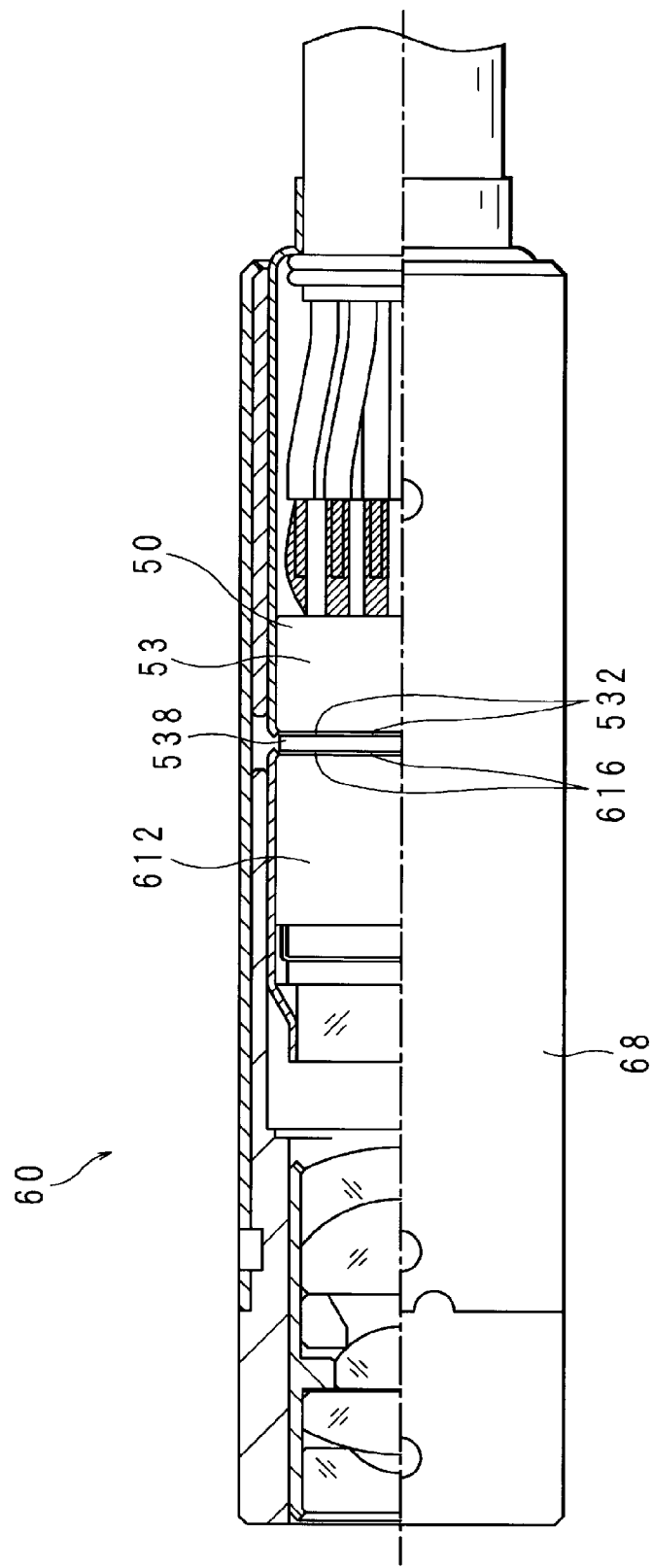
FIG. 31 is a half cross-sectional view of an imaging/cable unit of a fourth embodiment.

FIG. 31 is a half cross-sectional view of an imaging/cable unit 15 of the fourth embodiment. The imaging terminal 616 of the present embodiment is a protrusion having a flat end surface. An anisotropic conductive film 538 is sandwiched between the imaging terminal 616 and the connection terminal 532. The anisotropic conductive film 538 is a film that conducts in a thickness direction and does not conduct in an in-plane direction.

According to the present embodiment, it is possible to provide an endoscope 10 in which the imaging terminal 616 does not easily deteriorate even after multiple times of use.

[Fifth Embodiment]

The present embodiment relates to an endoscope 10 in which an abutting plate 58 supports an exterior cylinder 68. Descriptions regarding the same part as those of the first embodiment will be omitted.

Figure 32:
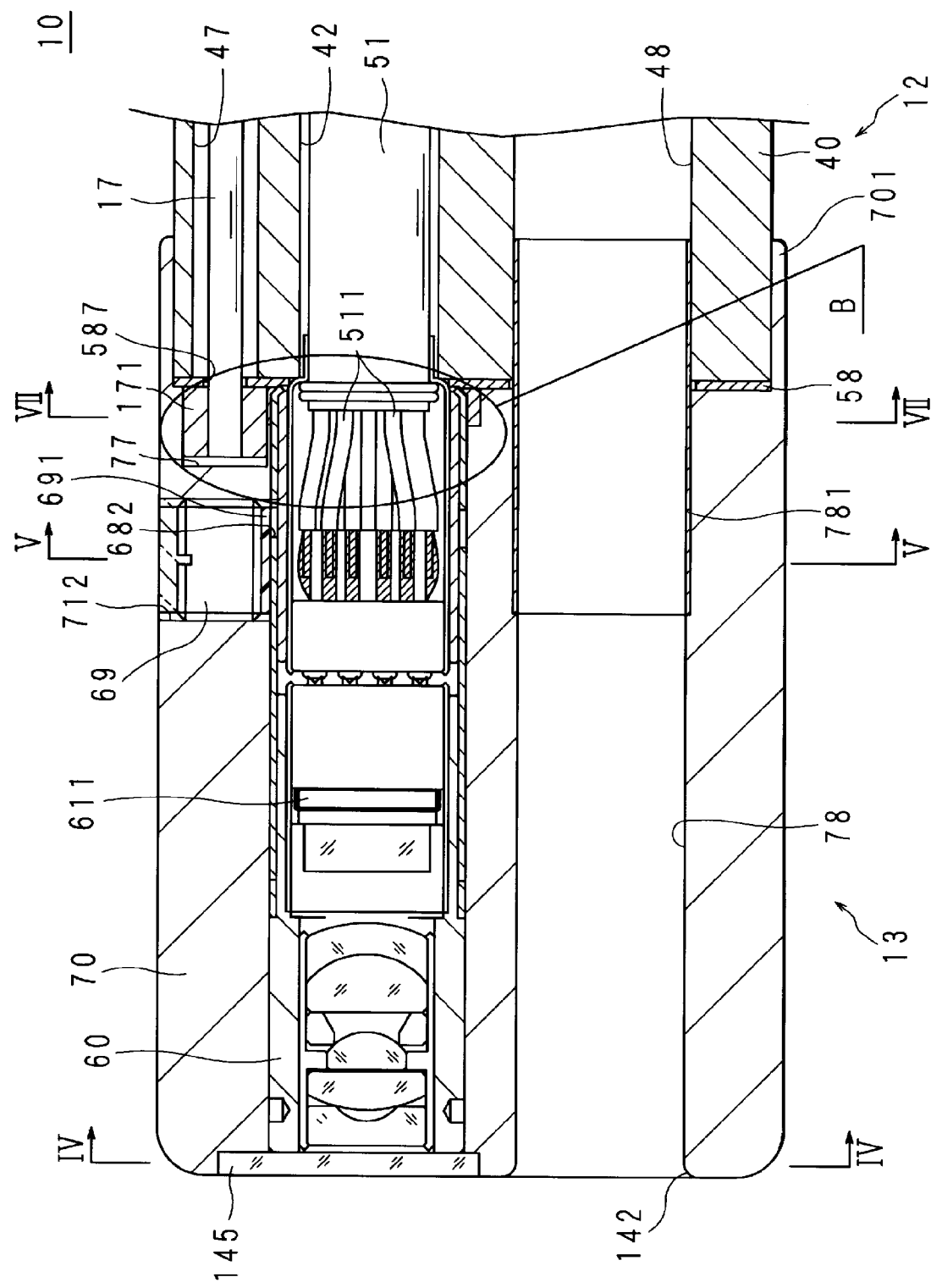
FIG. 32 is a cross-sectional view of an endoscope of a fifth embodiment.
Figure 33:
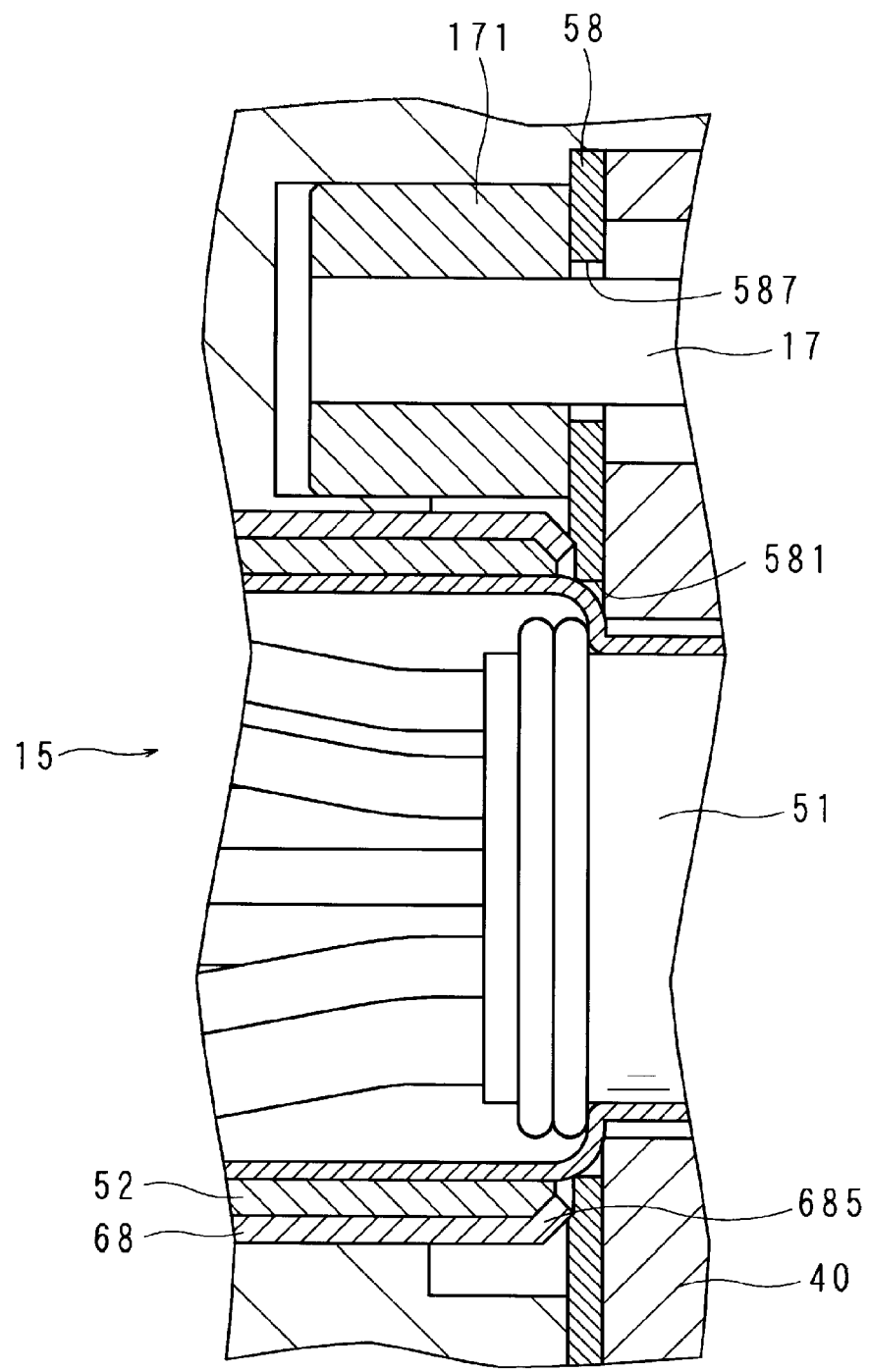
FIG. 33 is an enlarged view of Part B in FIG. 32.

FIG. 32 is a cross-sectional view of the endoscope 10 of the fifth embodiment. FIG. 33 is an enlarged view of Part B in FIG. 32. An inner dimension of a square hole 581 provided in the abutting plate 58 of the present embodiment is smaller than that of a caulked portion of an end portion of the exterior cylinder 68, and the caulked portion of the end portion of the exterior cylinder 68 is supported by the abutting plate 58, and thus does not move toward a multi-lumen tube 40.

Since a prismatic portion of an imaging/cable unit 15 is sandwiched between a window plate 145 and the abutting plate 58, a state of connection between an imaging terminal 616 and a connection terminal 532 is stably maintained even when a temperature change or a secular change occurs.

According to the present embodiment, it is possible to provide an endoscope 10 in which a state of connection between the imaging terminal 616 and the connection terminal 532 is stably maintained.

Technical features (constitutional requirements) described in the respective embodiments can be combined with each other, and new technical features can be formed with the combination.

The embodiments disclosed herein are exemplary in all respects, and it should be considered that the embodiments are not restrictive. The scope of the present invention is defined not by the above-described meaning but by claims, and intended to include all modifications within meaning and a scope equivalent to the claims.

Reference Signs List 10 endoscope
11 soft portion
12 bending section
13 distal tip piece
132 observation window
133 illumination window
136 light emitting element
14 insertion portion
141 jet outlet
142 channel outlet
143 air supply nozzle
144 water supply nozzle
145 window plate
15 imaging/cable unit
151 imaging/cable unit frame
16 bend preventing portion
17 bending wire
171 bending wire stopper
20 operation unit
21 bending knob
22 channel inlet
23 forceps plug
24 connector unit
25 universal cord
252 second cable assembly
253 second relay board
258 frame
259 attaching screw
26 connector case
27 scope connector
40 multi-lumen tube
42 cable hole
43 air supply hole
46 illumination hole
47 bending wire hole
48 channel hole
49 jet hole
50 cable assembly (cable)
51 cable bundle
511 cable strand
52 connection frame
53 connection block
532 connection terminal
535 insulating tube
538 anisotropic conductive film
55 first relay board
552 connection connector
553 land
554 attaching hole
58 abutting plate
581 square hole
582 jet hole 583 air supply hole
584 water supply hole
586 illumination hole
587 wire hole
588 channel hole
60 imaging unit
61 imaging frame
611 image sensor
612 imaging board
614 light-blocking mask
615 insulating tube
616 imaging terminal
617 image sensor assembly
618 stopper protrusion
619 claw hole
62 imaging lens assembly
621 imaging lens
622 imaging lens frame
623 filter
628 contact wall
68 exterior cylinder
681 cylinder notch
682 holding recess
685 bent portion
688 stopper hole
69 fixing screw
691 protection sheet
70 distal tip frame
701 distal tip frame edge
71 square hole (housing portion, through-hole)
711 air hole
712 communication hole
72 jet hole
721 jet pipe
73 air supply hole
731 air supply pipe
74 water supply hole
741 water supply pipe
75 window plate frame
76 illumination hole
761 illumination cable
77 wire stopper hole
78 channel hole
781 channel pipe
81 extrusion jig
82 claw jig

The invention claimed is:

1. An endoscope comprising:
an imaging unit including an image sensor and an optical component that forms an image of light incident from a first end surface on the image sensor;
a cable inserted into an insertion portion and having a first end connected to the imaging unit;
an exterior cylinder covering a connected portion between the imaging unit and the cable; and
a distal tip piece in which a housing portion having a shape fitted with a shape of the exterior cylinder is provided and which is arranged at a distal tip of the insertion portion, wherein
the imaging unit includes an imaging terminal arranged on a second end surface and connected to the image sensor,
the cable includes
a cable strand,
a connection block having a prismatic shape or square plate shape, and
a connection terminal that is arranged at a position corresponding to the imaging terminal on a first end surface of the connection block and that is connected to a first end of the cable strand,
the imaging terminal and the connection terminal are conductive, and
the imaging terminal of the imaging unit includes claws protruding toward the connection terminal of the cable, establishing a connection state with the connection terminal,
wherein the claws pierce the outer surface of the connection terminal to establish the connection state with the connection terminal.

2. The endoscope according to claim 1, wherein the distal tip piece includes a translucent window plate that covers the optical component.

3. The endoscope according to claim 2, wherein the window plate is bonded to the distal tip piece with an adhesive whose adhesive strength changes when a temperature changes.

4. The endoscope according to claim 1, wherein the imaging unit has a prismatic shape,
the exterior cylinder has a square cylinder shape, and
the housing portion is a square hole housing the exterior cylinder.

5. The endoscope according to claim 1, wherein
in the distal tip piece, a communication hole that communicates with the housing portion from an outer surface is provided,
the exterior cylinder has a holding recess that is a through-hole or a recess and is formed in a side surface of the exterior cylinder, and
the holding recess is arranged inside the communication hole at a position adjacent to an operation unit.

6. The endoscope according to claim 5, further comprising a fixing screw that is screwed into the communication hole to fix the exterior cylinder.

7. The endoscope according to claim 1, wherein
the cable includes a connection frame having a square cylinder shape and covering a side surface of the connection block and a connected portion between the connection terminal and the cable strand, and
the exterior cylinder
is fixed to a side surface of the imaging unit,
covers a side surface of the connection frame, and
has an inwardly bent portion at an end portion that is adjacent to the connection block.

8. The endoscope according to claim 7, wherein the bent portion is a caulked portion for fixing the exterior cylinder to the connection frame.

9. The endoscope according to claim 1, wherein
the imaging unit includes a stopper protrusion provided upright in the side surface, and
the exterior cylinder has a stopper hole that is engaged with the stopper protrusion.

10. The endoscope according to claim 1, wherein
the insertion portion has a cable hole into which the cable is inserted,
the cable includes a relay board connected to a second end and a connection connector mounted on the relay board, and
the connection connector and the relay board pass through the cable hole while being connected to the cable.

11. The endoscope according to claim 1, wherein the claws of the imaging terminal of the imaging unit establish a connection state with the connection terminal without sufficient deformation or scratching when piercing the connection terminal so as to render the imaging unit repeatedly usable in the endoscope.

12. The endoscope according to claim 1, wherein the material of which the imaging terminal is composed has a higher hardness than the material of which the connection terminal is composed, whereby the claws of the imaging terminal pierce the connection terminal without sufficient deformation or scratching so as to render the imaging unit repeatedly usable in the endoscope.

13. The endoscope according to claim 12, wherein the connection terminal is composed of solder or copper and the imaging terminal is composed of brass.

\* \* \* \* \*